United States Patent [19]
Sokatch et al.

[11] Patent Number: 5,656,483
[45] Date of Patent: Aug. 12, 1997

[54] **GENES ENCODING OPERON AND PROMOTER FOR BRANCHED CHAIN KETO ACID DEHYDROGENASE OF *PSEUDOMONAS PUTIDA* AND METHODS**

[75] Inventors: John R. Sokatch, Oklahoma City, Okla.; Pamela J. Sykes, Coromandel Valley, Australia; K. T. Madhusudhan, Cleveland, Ohio

[73] Assignee: Board of Regents of the University of Oklahoma, Norman, Okla.

[21] Appl. No.: 403,545

[22] Filed: Mar. 14, 1995

Related U.S. Application Data

[63] Continuation of Ser. No. 603,781, Oct. 19, 1990, abandoned, which is a continuation-in-part of Ser. No. 498,458, Mar. 21, 1990, abandoned, which is a continuation of Ser. No. 172,148, Mar. 23, 1988, abandoned.

[51] Int. Cl.$^6$ .................... C12N 5/10; C12N 15/52; C12N 15/63
[52] U.S. Cl. .................... 435/252.3; 435/320.1; 536/23.2
[58] Field of Search .................... 536/23.7, 23.2; 435/320.1, 252.3

[56] References Cited

PUBLICATIONS

Sykes et al., Abstr. Ann. Meeting Am. Soc. Microbiol. 85:117 1985.
Sykes et al., Fed. Proc. 44:1815 (1985).
Menard et al., Fed. Proc. 45:1533 (1986).
Burns et al., Eur. J. Biochem. 179:61–69 (1989).
Madhusudhan K.T. et al. 1990, *J. Bacteriol*, vol. 172 pp. 5655–5663.
Sokatch, J.R. et al. 1981, *J. Bacteriol*. vol. 148 pp. 639–646.
Burns, G. et al. 1988, *Eur. J. Biochem.* vol. 176 pp. 311–317.
Burns, G. et al. 1988, *Eur. J. Biochem.* vol. 176 pp. 165–169.
Sykes, P.J. et al. 1987, *J. Bacteriol.* vol. 169 pp. 1619–1625.
Yamisch-Pernon, C. et al. 1985, *Gene* vol. 33 pp. 103–119.
Soketch, J.R. et al. 1981. *J. Bacteriol*, vol. 148 pp. 647–652.
Bagdasarian, M. et al. 1981. *Gene* vol. 16 pp.237–247.
Sykes, P.J. et al. 1985. *J. Bacteriol.* vol. 162 pp. 203–208.
Lüthi, E. et al. 1986, *J. Gen. Microbiol.* vol. 132 pp. 2667–2675.
Inouge, S. et al. 1986. *J. Bacteriol.* vol. 166 pp. 739–745.
Minton, N.P. et al. 1983, *J. Bacteriol.* vol. 156 pp. 1222–1227.
Schell, M.A. 1983, *J. Bacteriol.* vol. 153 p. 822–829.
Madhusudhan, K.T. et al. (1990) *J. Bacteriol.* vol. 172 pp. 5655–5663.

*Primary Examiner*—Keith D. Hendricks
*Assistant Examiner*—Eric Grimes
*Attorney, Agent, or Firm*—Dunlap & Codding, P.C.

[57] ABSTRACT

DNA sequences coding for branched chain keto dehydrogenase, a promoter and branched chain keto dehydrogenase, and the promoter are disclosed. Also disclosed are recombinant vectors comprising one of the foregoing DNA sequences, transformed hosts comprising one of the foregoing recombinant vectors, and a method of making the polypeptide encoded by the DNA sequence.

4 Claims, 4 Drawing Sheets pJRS25, pJRS40, pJRS47, pJRS48 pJRS43, pJRS44, pJRS49, pJRS50 pSS1-2

1kb

GENES ENCODING OPERON AND PROMOTER FOR BRANCHED CHAIN KETO ACID DEHYDROGENASE OF *PSEUDOMONAS PUTIDA* AND METHODS

CROSS REFERENCE TO RELATED APPLICATIONS

This is a continuation of application Ser. No. 07/603,781 filed on Oct. 19, 1990, entitled "GENES ENCODING OPERON AND PROMOTER FOR BRANCHED CHAIN KETO ACID DEHYDROGENASE OF PSEUDOMONAS PUTIDA AND METHODS", now abandoned, which application is a continuation in part application of U.S. Ser. No. 07/498,458 filed Mar. 21, 1990 entitled MOLECULAR CLONING OF GENES ENCODING BRANCHED CHAIN KETO ACID DEHYDROGENASE OF PSEUDOMONAS PUTIDA, now abandoned, which is a continuation of U.S. Ser. No. 07/172,148 filed Mar. 23, 1988 of the same title, now abandoned.

GOVERNMENT SUPPORT

This invention was made with government support under Public Health Service grants AM21737 and GM30428 from the National Institutes of Health. The government has certain rights in this invention.

FIELD OF THE INVENTION

The present invention relates to DNA coding for branched chain keto dehydrogenase operon and promoter, and methods of use.

DESCRIPTION OF THE PREFERRED EMBODIMENTS

Figure 1:
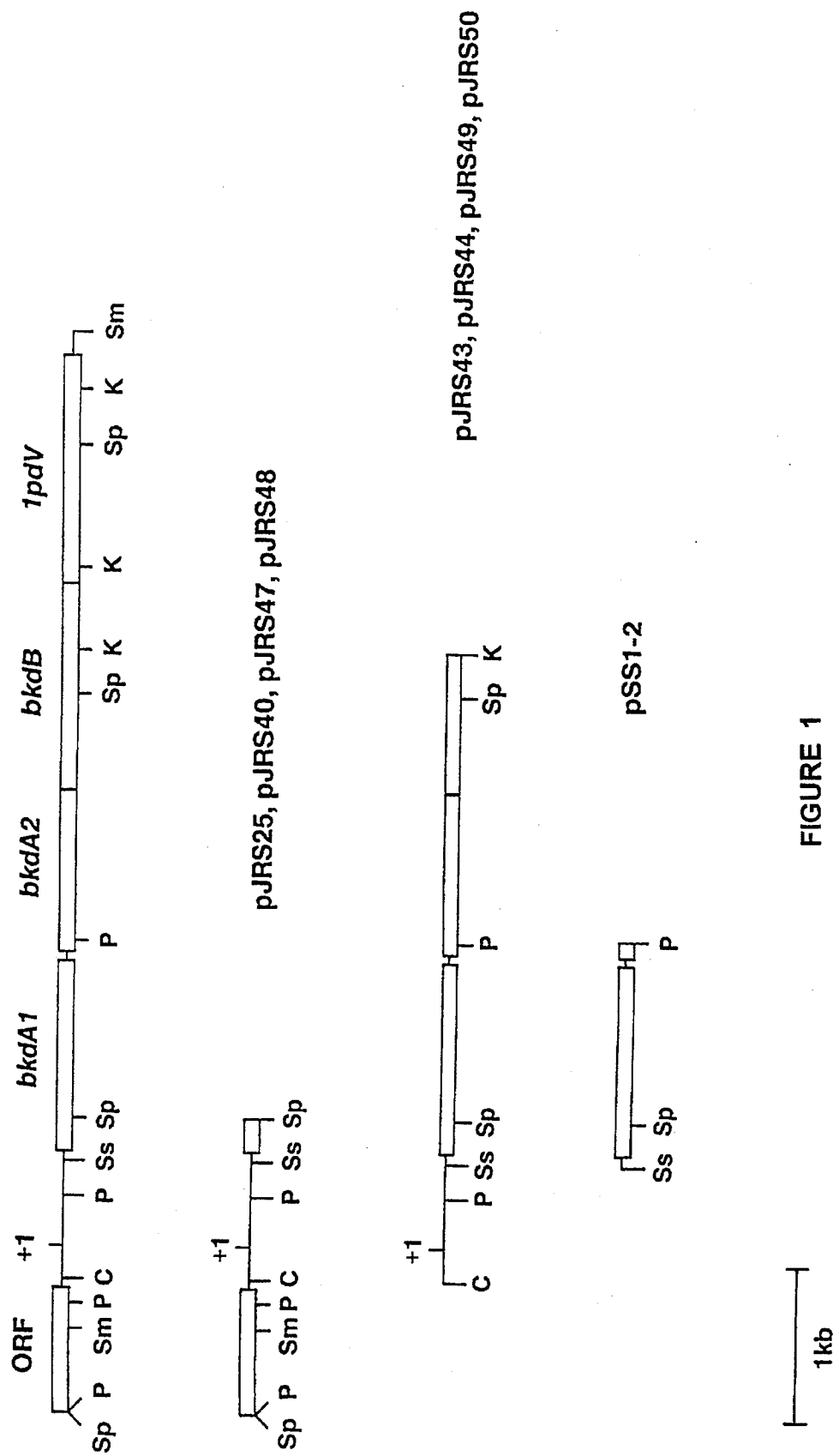
FIG. 1 shows a restriction map of the bkd operon (Sequence ID No. 1) and clones. The location of the transcriptional start of the operon a is +1. The structural genes are bkdA1=E1α, (Sequence ID No. 2) bkdA2=E1β, bkdB=E2, (Sequence ID No. 4) and lpdV=LPD-val (Sequence ID No. 4). ORF indicates the unidentified open (Sequence ID No. 3) reading frame on the strand opposite that encoding the bkd operon (Sequence ID No. 1). Abbreviations for the restriction enzyme sites are: C=ClaI; K=KpnI; P=PstI; sp=SphI; Ss=SstI; Sm=SmaI.

Branched chain keto acid dehydrogenase is a multienzyme complex which catalyzes the oxidation of branched chain keto acids formed by the transamination of branched chain amino acids. This enzyme is induced in *Pseudomonas putida* and *Pseudomonas aeruginosa* by growth in media containing branched chain amino acids or branched chain keto acids, the latter being the true inducers. Branched chain keto acid dehydrogenase purified from *P. putida* or *P. aeruginosa* consists of three functional components, E1 (Sequence ID No. 2 and Sequence ID No. 3), E2 (Sequence ID No. 4), and E3 (Sequence ID No. 5).

The E1 component (Sequence ID No. 2 and Sequence ID No. 3) consists of two nonidentical subunits, E1α (Sequence ID No. 2) and E1β (Sequence ID No. 4), and catalyzes the oxidative decarboxylation of the keto acid substrates. The E2 component (Sequence ID No. 4) contains covalently bound lipoic acid which is reduced by E1 and to which the acyl agroup becomes attached. The E3 component (Sequence ID No. 5) of Pseudomonas branched chain keto acid dehydrogenase is a specific lipoamide dehydrogenase named LPD-val since it is induced in media containing valine or other branched chain amino acids.

The present invention comprises the gene that encodes for branched chain keto acid dehydrogenase (hereafter "bkad gene") produced by recombinant DNA techniques. By using the recombinant bkad gene, branched chain keto acid dehydrogenase can now be economically produced.

The present invention also comprises the bkad gene and any promoter which expresses the gene of the present invention. One example of a promoter of the present invention is the promoter normally found in *Pseudomonas putida* which expresses the bkad gene (herafter "bkad promoter"). The bkad promoter (Sequence ID No. 6) may also be used to express homologous and heterologous genes in Pseudomonas for genes other than bkad genes.

The genus Pseudomonas can be a better host for use in recombinant DNA techniques than the genus Escherichia. Many genes expressed in *E. coli*, the usual host used for recombinant DNA procedures, produce proteins that are insoluble and improperly folded. In order to retrieve the protein of interest, the protein must be dissolved in denaturing agents and slowly allowed to refold. Rarely does the protein fold in the proper configuration due to the presence of granules, therefore, the advantage of over-expression is lost. In a preferred embodiment, genes expressed from the bkad promoter (Sequence ID No. 6) expressed in *Pseudomonas putida* at least ten-fold greater than when expressed from the β-lactamase promoter of pKT230 and 50–100 fold greater than in the wild type organism of *Pseudomonas putida*.

The gene of interest could be inserted immediately behind the bkad promoter (Sequence ID No. 6) and leader of the present invention which would control the expression of this gene. The resulting plasmid would then be transferred to a Pseudomonas host such as *Pseudomonas putida* grown in a simple medium such as L-broth, which would result in high expression of the gene of interest without forming granules.

Some examples of recombinant plasmids constructed in accordance with the present invention are pJRS54, pJRS55 and pSS1-1. pJRS54 comprises an insert of *Pseudomonas putida* genomic DNA comprising the promoter, leader, ribosome binding site and the four structural genes of the branched chain keto acid dehydrogenase operon. The vector is pUC19 and the host is *Escherichia coli* DH5α. pJRS54 has been deposited in the American Type Culture Collection at Rockville, Md. under number ATCC 68405.

pJRS55 comprises the promoter, leader, ribosome binding site and the coding sequence of the four N-terminal amino acids of the first protein encoded by the branched chain keto acid dehydrogenase operon. The vector is pKT240 and the host is *Escherichia coli* DH5α. pJRS55 has been deposited in the American Type Culture Collection at Rockville, Md. under number ATCC 68403.

pSS1-1 comprises the ribosome binding site and the four structural genes of the branched chain keto acid dehydrogenase operon. The vector is pKT230 and the host is *Pseudomonas putida* JS112. pSS1-1 has been deposited in the American Type Culture Collection at Rockville, Md. under number ATCC 68404. This plasmid may be used when a promoter other than the bkad promoter is to be used.

Branched chain keto acid dehydrogenase produced by the bkad gene of the present invention may be used to increase the yield of an end-product of a metabolic pathway by increasing the flow of precursors. For example, the avermectin group of antibiotics produced by *Streptomyces avermitilis* contain branched chain fatty acids that are formed by the action of branched chain keto acid dehydrogenase. The commerical preparation of the avermectin antibiotics can be increased by providing a sufficient amount of branched chain keto acid dehydrogenase. In a preferred embodiment, *Steptomyces avermitilis* can be transformed with pJRS54 in a multi-copy Steptomyces vector.

The following examples illustrate the practice of preferred embodiments of the present invention. However, the present invention is not limited to the examples set forth.

EXAMPLE 1

Materials and Methods

Bacterial strains, plasmids, phage and culture conditions.

The strains, plasmids and phage used are as follows:

TABLE 1

| Strain, plasmid, or phage | Relevant genotype or phenotype[a] | Source or reference |
| --- | --- | --- |
| *P. putida* | | |
| PpG2 | Wild type | I. C. Gunsalus |
| JS113 | bkdA1 (Sequence ID No. 2) bkdA2 (Sequence ID NO. 3) | Sykes, P. J., et al., "Conjugative mapping of pyruvate, 2-ketoglutarate and branched chain keto acid dehydrogenase genes in *Pseudomanas putida* mutants." J. Bacteriol. 162:203-208 (1985) |
| KT2440 | mt-2 hsdR1 (r⁻ m⁺) | Kohler, T., et al., "Involvement of *Pseudomonas putida* RpoN sigma factor in regulation of various metabolic functions." J. Bacteriol.171:4326-4333 (1989) |
| rpoN mutant | Km$^r$ rpoN⁻ | Kohler, T. et al., *Pseudomonas putida* RpoN sigma factor in regulation of various metabolic functions." J. Bacteriol.171:4326-4333 (1989) |
| *E. coli* | | |
| TB1 | ara lacZ δM15 δ(lac proAB) φ80 hsdR17 (r⁻ m⁺) strA | BRL |
| DH5α | F⁻φ80d lacZ δM15 δ(lacZYA-argF) U169 endA1 hsdR17 (r⁻ m⁺) recA1 1 gyrA relA1 | BRL |
| JM101 | δ(lac-proAB) supE thi [F', traD36, proAB, lacI$^q$Z δM15] | Yanisch-Perron, C., et al., "Improved M13 phage cloning vectors and host strains: nucleotide sequences of the M13mp18 and pUC19 vectors." Gene. 33:103–119 (1985) |
| Plasmids | | |
| pKT240 | IncQ mob⁺ Ap$^r$ Km$^r$ | Bagdasarian, M. M., et al., "Activity of the hybrid trp-lac (tac) promoter of *Escherichia coli* in *Pseudomonas putida*. Construction of broad-host-range, controlled-expression vectors." Gene. 26:273–282 (1983) |
| pJRS25 | bkd promoter (Sequence ID No. 6) in pUC19 same orientation as lacz | described herein |
| pJRS40 | bkd promoter (Sequence ID No. 6) in pUC19, opposite to lacZ | described herein |
| pJRS43 | bkd promoter (Sequence ID No. 6) with bkdA1 (Sequence ID No. 2) bkdA2 (Sequence ID No. 3) pUC19, opposite to lacZ | described herein |
| pJRS44 | bkd promoter (Sequence ID No. 6) with bkdA in pUC19, same as orientation as lacZ | described herein |
| pJRS47 | Same insert as pJRS25 and pJRS40 in pKT240, opposite to aph | described herein |
| pJRS48 | Same insert as JRS25 and pJRS40 in pKT240, same orientation as aph | described herein |
| pJRS49 | Same insert as pJRS43 and pJRS44 in pKT240, opposite to aph | described herein |
| pJRS50 | Same insert as pJRS43 and pJRS44 in pKT240 same orientation as aph | described herein |
| pRK2013 | ColE1 mob⁺ tra⁺ (RK2)Km$^r$ | Goldberg, J. B., et al., "Cloning and expression in *Pseudomonas aeruginosa* of a gene involved in the production of alginate." J. Bacteriol. 158:1115–1121 (1984) |
| pUC19 | Ap$^r$ | Yanisch-Perron, C., et al., "Improved |

TABLE 1-continued

| Strain, plasmid, or phage | Relevant genotype or phenotype* | Source or reference |
|---|---|---|
| | | M13 phage cloning vectors and host strains: nucleotide sequences of the M13mp18 and pUC19 vectors." Gene. 33:103–119 (1985) |
| Phage | | |
| M13mp19 | | Yanisch-Perron, C., et al., "Improved M13 phage cloning vectors and host strains: nucleotide sequences of the M13mp18 and pUC19 vectors." Gene. 33:103–119 (1985) |

*Gene designations for *P. putida* are: bkdA1 E1α subunit and bkdA2, E1β subunit of branched chain keto acid dehydrogenase.

The growth conditions and media used are described in Sykes, P. U. et al., "Molecular cloning of genes encoding branched chain keto acid dehydrogenase of *Psudomonas putida*", *J. Bacteriol.* 169: 1619–1625 (1987) and Sykes, P. J., et al., "Conjugative mapping of pyruvate, 2-ketoglutarate and branched chain keto acid dehydrogenase genes in *Pseudomonas putida* mutants", *J. Bacteriol.* 162: 203–208 (1985). Pseudomonas isolation agar was from DIFCO Laboratories.

RNA was prepared from *P. Putida* grown in a minimal medium with either 0.3% valine and 0.1% isoleucine (valine/isoleucine medium) according to the method described in Sykes, P. J., et al., "Conjugative mapping of pyruvate, 2-ketoglutarate and branched chain keto acid dehydrogenase genes in *Pseudomonas putida* mutants", *J. Bacteriol.* 162: 203–208 (1985), or 10 mM glucose as the sole carbon source or in L-broth according to Lennox, E. S., "Transduction of linked genetic characters of the host by bacteriophage P1", *Virol.* 1: 190–205 (1955).

GASV medium was used for mutants affected in keto acid dehydrogenases, including branched chain keto acid dehydrogenase and contains 10 mM glucose, 2 mM acetate, 2 mM succinate, 0.3% L-valine and 0.1% L-isoleucine according to the method described in Sykes, P. J. et al., "Molecular cloning of genes encoding branched chain keto acid dehydrogenase of *Pseudomonas putida*", *J. Bacteriol.* 169: 1619–1625 (1987). When antibiotic supplements were added, the final concentrations were (μg/ml): ampicillin, 200; kanamycin, 90; and carbenicillin, 2000.

Enzymes and chemicals.

Restriction endonucleases and other DNA enzymes were obtained from Promega Corporation or Bethesada Research Laboratories, Inc. The ($\tau$-$^{32}$P)dCTP, ($\alpha$-$^{32}$P)dATP were from New England Nuclear Corporation. Isopropyl-β-D-thiogalactopryanoside (IPTG), 5-bromo-4-chloro-3-indolyl-β-D-galactopyranoside (X-gal), RNase A, ampicillin, kanamycin and carbenicllin were from Sigma Chemical Co. All other chemicals were of analytical reagent grade.

Enzyme Assays.

The assay for E1 component (Sequence ID No. 2 and Sequence ID No. 3) of branched chain keto acid dehydrogenase was performed in the presence of excess E2 (Sequence ID No. 4) and LPD-val (Sequence ID No. 5). The latter two components were proved by a 90,000× g supernatant fraction of *E. coli* TB1 (pKRS3) according to the method described in Sykes, P. U. et al, "Molecular cloning of genes encoding branched chain keto acid dehydrogenase of *Pseudomonas putida*", *J. Bacteriol.* 169: 1619–1625 (1987).

The conditions of the assay for branched chain keto acid dehydrogenase are described in Sokatch, J. R. et al., "Purification of a branched chain keto acid dehydrogenase for *Pseudomonas putida*", *J. Bacteriol.* 148: 647–652 (1981). The assay for E1 (Sequence ID No. 2 and Sequence ID No. 3) activity used the same conditions except that the assay was supplemented with 300 μg of a 90,000× g supernatant fraction prepared from *E. coli* TB1 (pJRS3). This fraction supplies excess E2 (Sequence ID No. 4) and LPD-val (Sequence ID No. 5) so that the rate of NADH formation depends on amount of E1α and E1β (Sequence ID No. 3).

Nucleic acid preparations.

Plasmid and phage DNA were prepared according to the method of Maniatis, T, et al., *Molecular cloning: A Laboratory Manual*, 1987, Cold Spring Harbor Laboratory, Cold Spring Harbor, N. Y. RNA was prepared according to the method of Burns, G., et al., "Sequence analysis of the lpdV gene for lipoamide dehydrogenase of branched chain oxoacid dehydrogenase of *Pseudomonas putida*", *Eur. J. Biochem.* 179: 61–69. Nick translation of DNA was performed according to manufacturer's recommendations using a kit from Bethesda Research Laboratories. End labelling of synthetic oligonucleotides was performed according to the method of Maniatis, T, et al., *Molecular cloning: A Laboratory Manual*, 1987, Cold Spring Harbor Laboratory, Cold Spring Harbor, N.Y.

Screening of *P. putida* genomic library.

An SphI genomic library of *P. putida* DNA in pUC19 in *E. coli* TB1 was used. The nick translated probe for screening the library was prepared from pSS1-2 [see Burns, G., et al., "Similarity of the E1 subunits of branched chain-oxoacid dehydrogenase from *Pseudomonas putida* to the corresponding subunits of mammalian branched chain-oxoacid and pyruvate dehydrogenases", *Eur. J. Biochem.* 176: 311–317 (1988)] by digestion with Sst I and PstI.

This relased a 1.45 kb fragment of DNA that included bkdA1 (Sequence ID No. 2) and part of bkdA2 (Sequence ID No. 3). The library was plated on L-agar containing ampicillin and the colonies were lifted using Colony-Plaque screen (NEN Corporation). DNA fixation, hybridization and washing conditions were those suggested by the manufacturer.

Subcloning and DNA sequencing.

The genomic DNA insert from the positive clone, pJRS25, was excised from pUC19 by digesting the DNA with SphI and the excised fragment was cloned in both orientations into the SphI site of M13mp19. These clones were digested at the KpnI and BamHI sites of the vector, treated with ExoIII and S1 nucleases and ligated, yielding a set of ordered deletions according to the method described in Henikoff, S., "Unidirectional digestion with exonuclease III creates targeted breakpoints for DNA sequencing", *Gene* 28: 351–359 (1984), for DNA sequencing which was done using a Sequenase kit (US Biochemical Corporation).

To avoid band compressions due to high GC content, DITP was used in place of dGTP as suggested by the manufacturer. Samples were electrophoresed in 7M urea-6% acrylamide (acrylamide to bis acrylamide ration, 19:1) gels in 89 mM Tris-89 mM boric acid –2.5 mM EDTA, pH 8.3.

S1 nuclease and reverse transcriptase mapping.

A clone containing bases 1–1354 of the strand encoding the bkd operon in M13mp19 was used to prepare radiolabelled, single-stranded DNA according to the method described in Aldea, M. et al. "Transcript mapping using [³⁵S]DNA probes, trichloroacetate solvent and dideoxy sequencing ladders: a rapid method for identification of transcriptional start points", *Gene* 65: 101–110 (1988), to identify the start of transcription. A 17 mer universal primer was annealed to single-stranded DNA of the M13mp19 subclones and the complementary strand was synthesized using ($\alpha^{32}$P)dCTP, dNTPs and Klenow polymerase.

To minimize the amount of uncopied M13mp19 template, a 5 fold molar excess of primer and cold nucleotides were included in the synthesis reaction according to the method described in Calzone, F. J. et al., "Mapping of gene transcripts by nuclease protection assays and cDNA primer extension", *Methods Enzymol.* 152: 611–632 (1987).

RNA (50 µg), extracted from *P. putida* grown in valine/isoleucine or glucose synthetic media and labelled DNA (10,000 cpm) were mixed in 30 µl of hybridization buffer (0.4M NaCl, 0.2M PIPES, pH 6.5, 5 mM EDTA, 80% formamide) according to Debarbouille, M., et al., "Expression of the *Escherichia coli* malPO operon remains unaffected after drastic alteration of its promoter", *J. Bacteriol.* 153: 1221–1227 (1983). The solution was heated for 10 minutes at 75° C. and incubated at 40° C. overnight for hybridization of the DNA probe with branched chain keto acid dehydrogenase specific mRNA.

Unhybridized DNA was digested with 500 U of S1 nuclease in S1 buffer (0.25M NaCl, 30 mM potassium acetate, pH 4.5, 1 mM $ZnSO_4$, 5% glycerol) at 40° C. for 1 hours. Nucleic acids were extracted with phenol, precipitated with ethanol and the pellet dissolved in deionized formamide and tracking dyes. The solution was heated to denature nucleic acids then loaded on a sequencing gel along with dideoxy sequencing ladders for precise sizing.

Reverse transcriptase mapping was carried out according to the method described in Shelness, G. S., et al., "Apolipoprotein II messenger RNA: Transcriptional and splicing heterogeneity yields six 5'-untranslated leader sequences", *J. Biol. Chem.*, 259: 9929–9935 (1984). A synthetic oligonucleotide (Sequence ID No. 7), beginning 546 bp upstream of the branched chain keto acid dehydrogenase ATG initiation codon and complementary to the mRNA was used as primer. It was synthesized at the Molecular Biology Resource facility of the Saint Francis Hospital of Tulsa, Okla. The 5' end labelled primer (5,000–10,000 cpm) was combined with 50 µg of RNA from *P. putida* grown on valine/isoleucine in 50 µl of buffer (100 mM tris-HCl, pH 8.3, 10 mM $MgCl_2$, 120 mM KCl, 5 mM DTT, 1 mM deoxynucleotide triphosphates).

After the addition of 15 U of arian myelobastosis virus reverse transcriptase, samples were incubated for 1 hour at 42° C. and the reaction was stopped by bringing the temperature to 75° C. for 10 minutes. After cooling to 40° C., 5 µg of boiled RNAse A was added to this mixture and further incubated for 1 hour at 37° C. The nucleic acids were precipitated with ethanol and analyzed by electrophoresis as described above for S1 protection analysis.

Molecular cloning:

The insert containing the bkd promoter (Sequence ID No. 6) was excised from pJRS25 by digestion with SphI and inserted into pUC19. Two constructs were obtained, one with the insert in the same orientation as the lacZ, that is, the same as pJRS25, and a second, pJRS40, which had the insert in the opposite orientation to the lacZ.

In order to determine how much of the insert was required for promoter activity, a set of ordered deletions was prepared from these clones by digestion with ExoIII an S1 nucleases according to Henikoff, S., "Unidirectional digestion with exonuclease III creates targeted breakpoints for DNA sequencing", *Gene* 28: 351–359 (1984). The inserts were excised from the multiple cloning sites of pUC19 by digestion with EcoRI and HindIII, isolated by agarose gel electrophoresis, and inserted into pKT240, also digested with EcoRI and HindIII.

*E. coli* DH5α was the host for transformation and transformants were selected using L-agar containing ampicillin. These constructs were transferred from *E. coli* DH5α to *P. putida* PpG2 by tri-parental mating according to the method described in Goldberg, J. B. et al., "Cloning and expression in *Pseudomonas aeruginosa* of a gene involved in the production of alginate", *J. Bacteriol.* 158: 1115–1121 (1984), and the exconjugants were plated on Pseudomonas isolation agar containing carbenicillin.

Clones with bkdA1 (Sequence ID No. 2) and bkdA2 (Sequence ID No. 3) as the reporter genes for the bkd promoter (Sequence ID No. 6) were constructed from pSO2 (Sequence ID No. 3), and 18 kb cosmid clone in pLAFR1 which contains the entire bkd operon (Sequence ID No. 1) plus 18 kb of flanking sequence according to the method described in S. K. Oh, M. S. thesis, University of Oklahoma Health Sciences Center, Oklahoma City, Okla., 1989. The cosmid, pSO2, was digested with SmaI releasing a 6.8 kb fragment containing the entire operon which was inserted into the SmaI site of pUC19, yielding pJRS51.

The insert was removed from pJRS51 by digestion with ClaI and BamHI. The ClaI site is at base 828 (FIG. 1) and the BamHI site is in the polylinker of pUC19. The ends of the insert were blunted with Klenow fragment and deoxynucleotide triphosphates and the fragment cloned into the SmaI site of pUC19. The resulting plasmid was digested with KpnI, which cuts into bkdB (Sequence ID No. 4), leaving bkdA1 (Sequence ID No. 2) and bkdA2 (Sequence ID No. 3) intact and into the polylinker upstream of the operon (FIG. 1).

Two constructs were obtained, pJRS43 with the promoter (Sequence ID No. 6), bkdA1 (Sequence ID No. 2) and bkdA2 (Sequence ID No. 3) in the opposite orientation as lacZ and pPJRS44, with the insert in the same orientation as lacZ. The inserts were then isolated from pUC19 by digestion with EcoRI and HindIII and inserted into pKT240 similarly digested. Again, two constructs were obtained, pJRS49, which has the insert in the opposite orientation to the aph gene and pJRS50 which has the insert in the same orientation as aph. The constructs were then transferred from *E. coli* DH5α to *P. putida* JS113 by tri-parental mating using pRK2013 according to the method described in Goldberg, J. B. et al., "Cloning and expression in *Pseudomonas aeruginosa* of a gene involved in the production of alginate", *J. Bacteriol.* 158: 1115–1121 (1984).

RESULTS

Isolation of bkd promoter.

A SphI genomic library of *P. putida* DNA in pUC19 was screened using a 1.45 kb nick-translated SstI-PstI fragment of *P. putida* DNA from pSS1-2 which contained all of bkdA1 (Sequence ID No. 2) and part of bkdA2 (Sequence ID No. 3) (FIG. 1) according to the method used in Burns, G. et al., "Similarity of the E1 subunits of branched chain-oxoacid dehydrogenase from *Pseudomonas putida* to the corresponding subunits of mammalian branched chain-oxoacid and pyruvate dehydrogenases", *Eur. J. Biochem* 176: 311–317 (1988). Several positive colonies were identified during the initial screening which where further screened by restriction digestion of minipreparations, and Southern blotting usng the 1.45 kb probe. A clone containing 1.87 kb insert was obtained that contained 244 bp of bkdA1 gene (Sequence ID No. 2) and 1628 bp of upstream DNA. This clone was named pJRS25 and the restriction map of the insert is shown in FIG. 1.

Nucelotide sequence of pJRS25 insert.

The nucleotide sequence of bases 721–1679 of pJRS25 is shown in Table 2. pJRS25 contains the bkd promotor (Sequence ID No. 6) at bases 728–1628, and the initial portion of bkdA1 (Sequence ID No. 2) from bases 1629–1674.

bases 304–310 of Sequence ID No. 1, and there is another tandem repeat at bases 477–486 of Sequence ID No. 1 and bases 496–505 of Sequence ID No. 1.

There is a kind of symmetry beginning at bases 627–633 of Sequence ID No. 1 where the sequence is followed by its complement, bases 640–646 of Sequence ID No. 1. The GC content of the leader sequence (bases 775–1628, Table 2) is 56.7% which is distinctly lower than the 65.2% for the structural genes of the bkd operon (Sequence ID No. 1).

This agrees with the belief that RNA polymerase binds preferentially to AT rich regions of the promoter. A low GC

TABLE 2

```
721  CACCCCACGGGCCATCTGCAGGCGGCGGCCTTCGAGAAAGCCTTCGGCGGTCATCACCTT
     GTGGGGTGCCCGGTAGACGTCCGCCGCCGGAAGCTCTTTCGGAAGCCGCCAGTA
        V  G  R  A  M  Q  L  R  R  G  E  L  F  G  E  A  T  M

781  GCCGCGTGGGACGCCGTTGAGGTCGGGGGTGACGCATTCGATTTCATCGATGCCCTGGAG

841  CTGAGCGATGCTCATGACGCTTGTCCTTGTTGTTGTAGGCTGACAACAACATAGGCTGGG
                          ———————>  <———————

901  GGTGTTTAAAATATCAAGCAGCCTCTCGAACGCCTGGGGCCTCTTCTATCGCGCAAGGTC

961  ATGCCATTGGCCGGCAACGGCAAGGCTGTCTTGTAGCGCACCTGTTTCAAGGCAAAACTC
                              *
1021 GAGCGGATATTCGCCACACCCGGCAACCGGGTCAGGTAATCGAGAAACCGCTCCAGCGCC

1081 TGGATACTCGGCAGCAGTACCCGCAACAGGTAGTCCGGGTCGCCCGTCATCAGGTAGCAC
                     ———————>                      ———————>

1141 TCCATCACCTCGGGCCGTTCGGCAATTTCTTCCTCGAAGCGGTGCAGCGACTGCTCTACC

1201 TGTTTTTCCAGGCTGACATGGATGAACACATTCACATCCAGCCCCAACGCCTCGGGCGAC

1261 AACAAGGTCACCTGCTGGCGGATCACCCCCAGTTCTTCCATGGCCCGCACCCGGTTGAAA
                                        <———————

1321 CAGGGCGTGGGCGACAGGTTGACCGAGCGTGCCAGCTCGGCGTTGGTGATGCGGGCGTTT
     <———————

1381 TCCTGCAGGCTGTTGAGAATGCCGATATCGGTACGATCGAGTTTGCGCATGAGACAAAAT

1441 CACCGGTTTTTTGTGTTTATGCGGAATGTTTATCTGCCCCGCTCGGCAAAGGCAATCAAC
        ———————>  ———————>

1501 TTGAGAGAAAAATTCTCCTGCCGGACCACTAAGATGTAGGGGACGCTGACTTACCAGTCA

1561 CAAGCCGGTACTCAGCGGCGGCCGCTTCAGAGCTCACAAAAACAAATACCCGAGCGAGCG
                                                            SD

1621 TAAAAAGCATGAACGAGTACGCCCCCCTGCGTTTGCATGTGCCCGAGCCCACCGGCCGG   1679
           M  N  E  Y  A  P  L  R  L  H  V  P  E  P  T  G  R
```

The codon for the initiating methionine of bkdA1 (Sequence ID No. 2) starts at position 1629 and the translated amino acid sequence matched exactly that of Elα (Sequence ID No. 2). The nucleotide sequence of the strand containing bkdA1 (Sequence ID No. 2) was translated in all three frames but no additional open reading frames were found on that strand which means that there is a large non-coding segment of DNA upstream of bkdA1 (Sequence ID No. 2) (Table 2).

There is a region of dyad symmetry from bases 41–49 of Sequence ID No. 1 and 56–64 of Sequence ID No. 1 with a modest, but probably significant free energy of formation of −14 kcal. Bases 280–286 of Sequence ID No. 1 repeat at content of the promoter region might also contribute to promoter strength by providing less resistance to DNA unwinding. Similar observations of low GC content for Pseudomonas promoter were made in the case of the algD and nah and sal promoters.

Figure 2:
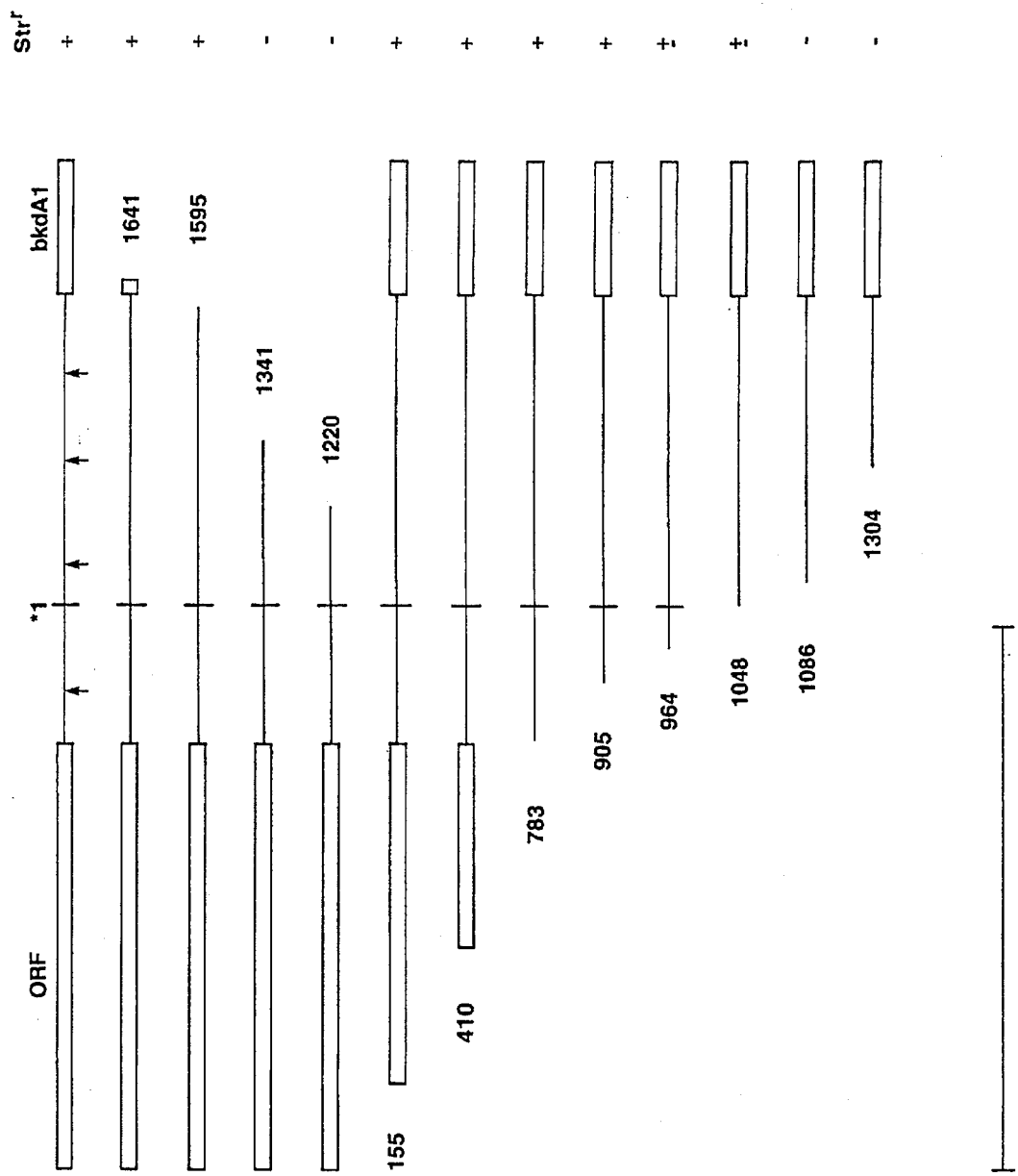
FIG. 2 shows the effect of deletions in the promoter region on bkd promoter (Sequence ID No. 6) activity. Streptomycin resistance was determined by growth on L-agar plus 8 mg streptomycin/ml. Numbers designated either the first (left) or last (right) base of the deletion clone as numbered in Table 2.

The strand opposite that encoding the branched chain keto acid dehydrogenase operon was translated into three reading frames and an open reading frame was found starting at 774 bp (FIG. 2). However, there does not seem to be a strong ribosome binding site preceding the start codon. This reading frame encoded 258 amino acids without a stop codon and the codon usage was consistent with that of other Pseudomonas genes.

The amino acid sequence was compared with the amino acid sequences of known regulatory proteins of bacteria in the Protein Information Resource data base, but no significant homology was found. However, a search by FASTP according to the method of Lipman, D. J. et al., "Rapid and sensitive protein similarity searches", *Science* 227: 1435–1441 (1985), showed some homology with several glutamine synthetases ranging from 22–31% identity over a span of about 130 amino acids, and always to the same part of glutamine sythetase, residues 175–305.

Transcriptional start of the bkd operon (Sequence ID No. 1).

The approximate start of the bkd transcript was first determined by S1 nuclease protection experiments. A single-stranded DNA template in M13mp19 was constructed by ExoIII nuclease digestion according to the method described in Henikoff, S., "Unidirectional digestion with exonuclease III creates targeted breakpoints for DNA sequencing", *Gene* 28: 351–359 (1984) which included bases 1–1354 of the pJRS25 insert. The M13 sequencing primer was annealed to the single-stranded DNA, and the complementary strand was synthesized using Klenow polymerase, dNTPs and ($\alpha^{32}$P)dCTP.

The radioactive DNA probe was hybridized to total cellular RNA extracted from *P. putida* grown in valine/isoleucine medium followed by treatment with a single-strand-specific S1 nuclease to destroy unprotected probe sequences according to the methods in Aldea, M., et al., "Transcript mapping using [$^{35}$S]DNA probes, trichloroacetate solvent and dideoxy sequencing ladders: a rapid method for identification of transcriptional start points", *Gene* 65: 101–110 (1988) and Calzone, F. J., et al., "Mappng of gene transcripts by nuclease protection assays and cDNA primer extension", *Methods Enzymol.* 152: 611–632 (1987).

These experiments show that the transcriptional start of the bkd operon (Sequence ID No. 1) was located about 600 bases upstream from the translational start. In order to locate the transcriptional start precisely, reverse transcriptase mapping was done by primer extension. A 15 mer oligonucleotide was constructed complementary to bases 1083–1097, i.e., 59 bp downstream from the start of transcription (Table 2). The end-labelled primer was hybridized to cellular RNA from *P. putida* PpG2 grown on valine/isoleucine medium and extended to the length of branched chain keto acid dehydrogenase mRNA with avian myeloblastosis virus reverse transcriptase.

The product was electrophoresed alongside dideoxy sequencing reaction mixtures using the same oligonucleotide primer (FIG. 2). A singles transcript was obtained, the mobility of which corresponded to base number 1037 of the pJRS25 insert. Therefore, the first base of the transcript is a cytidine nucleotide which means that the distance between the transcriptional and translational start is 592 bp.

In order to find the transcriptional initiation site of the message for the unknown open reading frame on the opposite strand, reverse transcriptase mapping was done using a 18 mer oligonucleotide that hybridized between 1097 and 1115 bp on the opposite strand (FIG. 2). The end-labelled oligonucleotide was annealed to RNA extracted from *P. putida* grown on L broth and minimal medium containing glucose or valine/isoleucine as the carbon sources.

No primer extension was evidenced after denaturing gel electrophoresis, indicating that there may not be a transcript or the transcript was not produced under the conditions which the cells were grown. Thus it is not clear if we are dealing with two promoters or if the bkd promoter is bidirectional.

Expression from the bkd promoter (Sequence ID No. 6).

The promoter activity of the insert of *P. putida* DNA in pJRS25 was studied using pKT240 which has a promoterless aminoglycoside phosphotransferase (aph) gene. When a DNA fragment containing a promoter is cloned in the correct orientation upstream of the aph gene, the host cell becomes streptomycin resistant.

The entire insert of pJRS25 was cloned into pKT240 in both orientations yielding pJRS47, with the insert opposed to aph, and pJRS48, with the insert in the same orientation as aph (Table 1). *E. coli* DH5α containing either pJRS47 or pJRS48 did not grow on L agar containing streptomycin at concentrations of 0.3 to 0.5 mg/ml indicating that *E. coli* does not read the bkd promoter (Sequence ID No. 6) well.

pJRS47 and pJRS48 were then mobilized from *E. coli* DH5α to *P. putida* PpG2 by tri-parental mating according to the method described in Goldberg, J. B. et al., "Cloning and expression in *Pseudomonas aeruginosa* of a gene involved in the production of alginate", *J. Bacteriol.* 158: 115–1121 (1984). The exconjugants were replica-plated on minimal medium containing valine/isoleucine or glucose as the carbon source plus various concentrations of streptomycin.

*P. putida* PpG2 containing either pJRS47 or pJRS48 was resistant to streptomycin at concentrations up to 10 mg/ml in both enriched and minimal media with either glucose or valine/isoleucine carbon sources. These results indicate the promoter was read in both directions and that streptomycin resistance was constitutive (FIG. 2). The finding that streptomycin resistance was not inducible strongly favors negative regulation of the bkd operon (Sequence ID No. 1).

*E. coli* DH5α and *P. putida* PpG2 (pKT240) did not grow at streptomycin concentrations beyond 0.25 and 2 mg/ml respectively. Expression of streptomycin resistance from pJRS47 was not expected, and this result suggests the presence of another promoter, possibly for the expression of the unidentified open reading frame on the strand opposite that of the bkd operon (Sequence ID No. 1) or that the bkd promoter (Sequence ID No. 6) is bidirectional.

A series of ordered deletions were created where the insert isolated from pJRS25 was shortened from both ends and then introduced into pKT240 to see what effect this had on promoter activity (FIG. 2). There is a span of about 550 bp which is essential from promoter activity in *P. putida* which begins 100 bp upstream of the start of transcription and ends 450 bp downstream from the start of transcription.

The two tandem repeats and the one dyad repeat downstream of the start are included in this essential region. However, the dyad repeat about 200 bp upstream of the start of transcription is not included. Perhaps this latter structure is involved in the expression of the unidentified open reading frame.

Expression of the bkd operon (Sequence ID No. 1) does not require the rpoN gene product.

Four deletion clones were mobilized into *P. putida* KT2440 and into the rpoN mutant. Two of the clones, those beginning at bases 783 and 905 (FIG. 2) conferred streptomycin resistance to both *P. putida* KT2440 and it rpoN mutant. The other two clones, those beginning at bases 1086 and 1304 (FIG. 2) failed to confer streptomycin resistance to either strain of *P. putida* KT2440.

In addition, the rpoN mutant of *P. putida* KT2440 is able to grow in synthetic medium with 2-ketoisovalerate as the sole carbon source, so it is clear that the rpoN sigma factor is not required for expression of branched chain keto acid dehydrogenase. As a control, it was confirmed that the rpoN mutant cannot grow in medium with valine/isoleucine as the carbon source, hence RpoN is required either for transport or transamination of branched chain amino acids.

Expression of bkdA1 (Sequence ID No. 2) and bkdA2 (Sequence ID No. 3) from the bkd promoter (Sequence ID No. 6).

In order to study the expression of the bkd operon, (Sequence ID No. 1) pJRS49 and pJRS50 were constructed (FIG. 1) which contain the bkd promoter (Sequence ID No. 6), bkdA1, (Sequence ID No. 2) and bkdA2 (Sequence ID No. 3) and part of bkdB (Sequence ID No. 4) in both orientations with respect to aph of pKT240. In these constructs, streptomycin resistance depends on the strength of the promoter upstream of aph and all are carbenicillin resistant due to the β-lactamase gene which is constitutively expressed.

pJRS43 and pJRS44 were transferred to P. putida JS113, a bkdA mutant, and plated on several media. P. putida JS113, a bkdA mutant, and plated on several media. P. putida JS113 containing either pJRS49 or pJRS50 grew on L-agar plus 8 mg/ml of streptomycin, however, P. putida JS113 (pJRS50), was more resistant to streptomycin than P. putida carrying pJRS49. These results show that read-through to aph occurred in both orientations.

P. putida JS113 (pJRS50) grew on valine/isoleucine agar plus streptomycin therefore the insert complemented the mutation in P. putida JS113. However, P. putida JS113 (pJRS49) did not grow on valine/isoleucine agar containing either carbenicillin or streptomycin for reasons which are not clear, but may be related to interference by these antibiotics with expression of the clone bkd genes.

In order to measure the level of expression of bkdA1 (Sequence ID No. 2) and bkdA2 (Sequence ID No. 3) from the bkd promoter, (Sequence ID No. 6) E1 enzyme assays were performed on 90,000× g supernatant fractions prepared from cultures grown in the media shown in Table 3.

high expression of bkdA1 (Sequence ID No. 2) and bkdA2 (Sequence ID No. 3) in P. putida JS113 containing either pJRS49 or pJRS50 grown in L-broth indicating that expression was constitutive as was streptomycin resistance in the case of P. putida PpG2 (pJRS48).

The level of E1 (Sequence ID No. 2 and Sequence ID No. 3) activity was surprisingly high compared to extracts of P. putida PpG2 grown in Valine/sioleucine medium (Table 3). Thus expression of bkdA1 (Sequence ID No. 2) and bkdA2 (Sequence ID No. 3) from P. putida JS113 (pJRS50) was nearly 40 times that obtained in P. putida PpG2 which seems to be much higher than could be accounted for by copy number alone.

When P. putida JS113 (pJRS50) was grown in valine/isoleucine medium, the specific activity was about twice that obtained in L-broth. These results also suggest that the bkd operon (Sequence ID No. 1) is negatively regulated, probably by a small amount of endogenous repressor which is titrated by the multiple copies of pJRS50 in the cell.

Again, P. putida JS113 (pJRS49), did not grow in this medium suggesting that bkdA1 (Sequence ID No. 2) and bkdA2 (Sequence ID No. 3) were not expressed. bkdA1 (Sequence ID No. 2) and bkdA2 (Sequence ID No. 3) expression was repressed by glucose (Table 3). It is pertinent to note that pseudomonads do not contain appreciable amounts of cAMP.

EXAMPLE 2

Materials and Methods

Bacterial strains and plasmids. The P. putida strains and plasmids used in this study are listed in Table 4.

TABLE 3

Expression of structural genes for E1 subunits (Sequence ID No. 2 and Sequence ID No. 3 branched chain keto acid dehydrogenase

| organism and medium[a] | pKT240 | Plasmid pJRS50 | pJRS49 |
|---|---|---|---|
| | | Specific activity[b] | |
| E. coli DH5α GASV | 0 | 0.014 | 0.018 |
| P. putida JS113 | | | |
| L broth | 0.009 | 2.37 | 2.59 |
| L broth + valine/isoleucine | 0.0007 | 2.68 | 1.50 |
| Minimal medium + valine/isoleucine | ND[c] | 5.23 | ND[c] |
| Minimal medium + glucose | 0.004 | 0.133 | 1.10 |

[a]Compositions of media are given in Materials and Methods.
[b]Specific activity is μmoles of NADH/min/mg protein. All assays of E1 (Sequence ID No. 2 and Sequence ID No. 3) were done by supplementing with excess E2 (Sequence ID No. 4) and LPD-val (Sequence ID NO. 5).
[c]Does not grow in this medium.
[d]The specific activities of P. putida grown in L broth, L broth + valine/isoleucine, minimal medium + glucose and minimal medium + valine/isoleucine were 0.010, 0.010, 0.004 and 0.063 respectively. Extracts of P. putida PpG2 (pKT240) and P. putida PgG2 (pJRS48) in L broth gave specific activities of 0.032 and 0.033 respectively.

There was very little expression of bkdA1 (Sequence ID No. 2) and bkdA2 (Sequence ID No. 3) in E. coli DH5α containing either pJRS49 or pJRS50. However, there was

TABLE 4

| Strains of P. putida | | |
|---|---|---|
| Strain and plasmid | Genotype[a] description or | Source |
| P. putida | | |
| PpG2 | Wild type | I. C. Gunsalus |
| JS112 | bkdAB 1pdV (Sequence ID NOS. 2,3,4, and 5) | Sykes, P. J., et al., "Conjugative mapping of pyruvate, 2-ketoglutarate, and branched chain keto acid dehydrogenase genes in Pseudomonas putida mutants." J. Bacteriol.162:203-208 (1985) |
| JS113 | bkdA (Sequence ID NO. 1 and Sequence ID NO. 2) | Sykes, P. J., et al., "Conjugative mapping of pyruvate, 2-ketoglutarate, and branched chain keto acid dehydrogenase genes in Pseudomonas putida mutants." J. Bacteriol. 162:203-208 (1985) |
| JS287 | 1pdV (Sequence ID NO. 5) | Sokatch, J. R., et al., "Mutations affecting lipoamide dehydrogenases of Pseudomonas putida." J. |

TABLE 4-continued

Strains of *P. putida*

| Strain and plasmid | Genotype[a] description or | Source |
|---|---|---|
| JS326 | bkdAB 1pdV (Sequence ID NOS. 2,3,4, and 5) | Bacteriol. 153:969-975 (1983) Sykes, P. J., et al., "Conjugative mapping of pyruvate, 2-ketoglutarate, and branched chain keto acid dehydrogenase genes in *Pseudomonas putida* mutants." J. Bacteriol. 162:203-208 (1985) |
| PRS2003 | pKT230 catB Kan[r] Str[r] | M. Shanley |
| Plasmids | | |
| pKT230 | Derived from RSF1010 and pACYC1771 | Basdarian, M. et al. "Specific purpose plasmid cloning vecotrs II. Broad host range, copy number RSF 1010 - derived vectors, and a host-vector system fro gene cloning Pseudomonas" Gene 16:237–247 (1981). |
| pJRS1 | bkdAB 1pdV (Sequence ID NOS. 2,3,4, and 5) in pUC18 | described herein |
| pJRS2 | bkdAB 1pdV (Sequence ID NOS. 2,3,4, and 5) in pUC19 | described herein |
| pJRS3 | bkdB 1pdV (Sequence ID NOS. 4 and 5) in pUC19 | described herein |
| pJRS4 | bkdAB 1pdV (Sequence ID NOS. 2,3,4, and 5) in pUC18 | described herein |
| pJRS10 | bkdA (Sequence ID NOS. 1 and 2) in pUC18 | described herein |
| pJRS23 | 1pdV (Sequence ID NO. 5) in pUC18 | described herein |
| pJRS24 | bkdbB (Sequence ID NO. 4) in pUC19 | described herein |

[a]Gene designations for strains and plasmids in this TABLE are bkdAB, E1 and E2 subunits of branched chain keto acid dehydrogenase; 1pdV, LPD-Val (E3 subunit); catB, cis,cis-muconate lactonizing enzyme; Kan, kanamycin; Str, streptomycin.

Branched chain keto acid dehydrogenase mutants listed in Table 4 cannot grow on the valine-isoleucine agar described in the next paragraph. The strains of *E. coli* used were JM109 [Yanish-Perron, C., et al., "Improved M13 phage cloning vectors and host strains: nucleotide sequences of the M13mp18 and pUC19 vectors", *Gene.* 33: 103–119 (1985)], HB101 [Boyer, H. W. et al., "A complementary analysis of the restriction and modifications of DNA in *Escherichia coli*", *J. Mol. Biol.* 141: 459–427 (1969)], and TB1 which was obtained from Bethesda Research Laboratories, Inc. (Gaithersburg, Md.). TB1 is similar to JM83 except that TB1 is hsdR hsdM[+]. The plasmid vector pKT230 was described by Bagdasarian et al., "Specific purpose plasmid cloning vectors," *Gene* 16: 237–247 (1981) and was provided by Mark Shanley, Department of Biology, Yale University.

Media. Valine-isoleucine agar contained 0.3% L-valine and 0.1% L-isoleucine in the basal medium as described in Marshall, V. P., et al., "Regulation of valine catabolism in *Pseudomonas putida.*" *J. Bacteriol.* 110: 1073–1081 (1972). Basal medium free of ammonium ion was obtained by omitting ammonium sulfate from the basal G solution. To test the inducibility of subunits of the complex in organisms unable to grow on valine-isoleucine agar, we used GASV medium. GASV medium contains 10 mM glucose, 2 mM acetate, 2 mM succinate, 0.3% valine, and 0.1% isoleucine. Valine is deaminated to 2-ketoisovalerate, the inducer of branched chain keto acid dehydrogenase, allowing expression of branched chain keto acid dehydrogenase. GAS medium lacks valine and isoleucine and was used to grow keto acid dehydrogenase mutants which might require acetate or succinate for growth as described in Guest, J. R., "Aspects of the molecular biology of lipoamide dehydrogenase", *Adv. Neurol.* 21: 219–244 (1978). L broth was used as described in Lennox, E. S., "Transduction of linked genetic characters of the host of phage P1." *Virology.* 1: 190–206 (1955) and 2×YT medium as described in Miller, J. H., "Experiments in molecular genetics." *Cold Spring Harbor Laboratory,* Cold Spring Harbor, N.Y. (1976). When antibiotic supplements were used, the final concentrations were (micrograms per milliliter): streptomycin, 100; kanamycin, 90; ampicillin, 200.

DNA preparation. pKT230 was isolated from *P. putida* PRS2003 grown in 800 ml of L broth plus kanamycin by using two successive cesium chloride-ethidium bromide centrifugations of cleared lysates by the method of Clewell, D. B., et al., "Properties of a supercoiled deoxyribonucleic acid-protein relaxation complex and strand specificity of the relaxation event", *Biochemistry* 9: 4428–4440 (1970). *P. putida* chromosomal DNA was isolated from a single cesium chloride-ethidium bromide centrifugation by the same method as for plasmid preparation with omission of the sodium chloride precipitation step. DNA restriction fragments were separated by electrophoresis in 0.8% agarose gel.

Cloning procedures. A limited digest of *P. putida* chromosomal DNA by EcoRI and SstI produced a majority of fragments in the 5- to 15-kilobase (kb) size range. This was mixed with a complete EcoRI-SstI digest of pKT230 with chromosome-to-vector DNA ratios of 10:1 and ligated with T4 ligase. EcoRI-SstI digestion of pKT230 inactivates the streptomycin resistance gene, but leaves the β-lactamase promoter, which controls this gene, intact. Recombinant plasmids were Km[r] and Sm[s]. The amount of DNA used in the ligations and transformations ranged from 0.06 to 0.2 μg. Ligation was done in a total volume of 50 μl containing 2 U of T4 ligase, and the mixture was left overnight at 14° C. The transformation procedure used for *P. putida* was that described by Bagdasarian, M. et al., "Host: vector systems for gene cloning in Pseudomonas." *Curr. Top. Microbiol. Immunol.* 96: 47–67 (1982). Direct selection for recombinant molecules was achieved by complementation of *P. putida* branched chain keto acid dehydrogenase mutants listed in Table 4 for growth on valine-isoleucine medium and sensitivity to streptomycin. pSS1 and pSS1-1, which are recombinant derivatives of pKT230, were created in this fashion.

pJRS1 was created by digesting pSS1-1 with SstI and inserting the fragment into pUC18 also digested with SstI (FIG. 3). pJRS2 was created by digesting pJRS1 with EcoRI and HindIII which cut into the polylinker of pUC18, removing the insert of *P. putida* DNA which was ligated into pUC19 similarly digested. This procedure produced plasmids with inserts of *P. putida* DNA in opposite orientations.

pJRS3 was constructed from a PstI-SalI digest of pJRS2, and the resulting fragment was inserted into the polylinker of pUC19.

pJRS4 was constructed from pJRS1 by digestion with EcoRI and ClaI, which released a 6-kb fragment and left 1.8 kb of DNA still attached to pUC18. The 1.8-kb fragment was released by digestion with AccI which also created a sticky end in the polylinker compatible with ClaI. The 6-kb fragment was then ligated into pUC18 with EcoRI-ClaI sticky ends, yielding pJRS4.

pJRS10 was created by digestion of pJRS1 with KpnI which removed 4.5 kp of *P. putida* DNA. The remaining DNA (pUC18 plus insert of 3.3 kb) was then religated, yielding pJRS10.

pJRS23 was made by digesting the *P. putida* DNA insert of pJRS1 with Bal 31 so that deletions were created from the SstI restriction site at the E1 end of the coding region according to the method of Gilmore, M. S., et al., "A new strategy for ordered DNA sequencing based on a newer method for the rapid purification of near-milligram quantities of a cloned restriction fragment", *Gene Anal. Tech.* 2: 108–114 (1985). The resulting DNA fragment contained a blunt end and a HindIII sticky end which was ligated into pUC18. This plasmid, pJRS21, was cut with SalI and EcoRI which released 2.3 kb of DNA. The remaining 2.9 kb of DNA was ligated into pUC18.

pJRS24 was obtained by digesting the polylinker of pJRS3 with BamHI and SstI and treating with ExoIII and S1 nucleases according to the method of Henikoff, S., "Unidirectional digestion with exonuclease III creates targeted breakpoints for DNA sequencing", *Gene* 28: 351–359 (1984) and recircularizing the shortened plasmid with T4 ligase. The 3' overhang left by SstI protected the vector from digestion with ExoIII, while the 5' overhang left by BamHI allowed pJRS3 to be shortened from the E3 end, leaving only the E2 gene.

Genomic DNA-plasmid DNA hybridizations were done as described by Southern, E. M., "Detection of specific sequences among DNA fragments separated by gel electrophoresis." *J. Mol. Biol.* 98: 503–517 (1975), using 0.33 μg of pSS1-1, pJRS1, or pJRS2 ($1.3 \times 10^7$ cpm/μg) and 5 to 6 μg of *E. coli, P. aeruginosa*, or *P. putida* DNA digested with EcoRI. To reduce hybridization with vector DNA, we included 0.6 μg of cold pKT230 or pUC18.

Minicells. The minicell strain used in these experiments was *E. coli* ×925 which was obtained from Roy Curtiss. The experiment was performed essentially as described by Clarke-Curtiss, J. E., et al., "Analysis of recombinant DNA using *Escherichia coli* minicells." *Methods Enzymol.* 101: 347–362 (1983), using 5 μCi of [$^{35}$S]methionine and with electrophoresis in 7.5% cross-linked polyacrylamide. Minicell cultures were grown in GASV medium since *E. coli* does not grow in valine-isoleucine medium.

In vitro transcription-translation. The procaryotic DNA-directed translation kit was purchased from Amersham and used as described in their instructions with 2.5 μg of DNA template for each reaction.

Enzyme assays. Preparation of extracts and the assays for branched chain keto acid dehydrogenase and lipoamide dehydrogenase have been described previously. The E1 (Sequences ID No. 2 and No. 3) and E2 (Sequence ID No. 4) assays were performed according to the method described in Sykes, P. J., et al., "Conjugative mapping of pyruvate, 2-ketoglutarate, and branched chain keto acid dehydrogenase genes in *Pseudomonas putida* mutants", *J. Bacteriol.* 162: 203–208 (1985), and McCully, V. et al., "Resolution of branched chain oxo acid dehydrogenase complex of *Pseudomonas aeruginosa* PAO", *Biochem. J.* 233: 737–742 (1986).

Stability of pSS1-1 in *P. putida*. Cultures of strain JS287 transformed with pKT230 and pSS1-1 were grown overnight in 4 ml of L broth plus kanamycin, and 0.1 ml of this culture was used to inoculate another 4 ml of L broth without kanamycin. Dilutions of overnight cultures were plated onto L agar, and resulting colonies were replica plated onto valine-isoleucine agar, valine-isoleucine agar plus kanamycin, and L agar plus kanamycin. Colonies growing on valine-isoleucine agar plus kanamycin were scored as carrying pSS1-1, colonies growing on valine-isoleucine agar without kanamycin were revertants, and those growing on L agar plus kanamycin but not valine-isoleucine agar plus kanamycin were carrying pKT230. These numbers were compared with the total number of colonies growing on L agar without kanamycin which included cells which had lost their plasmids.

RESULTS

Figure 3:
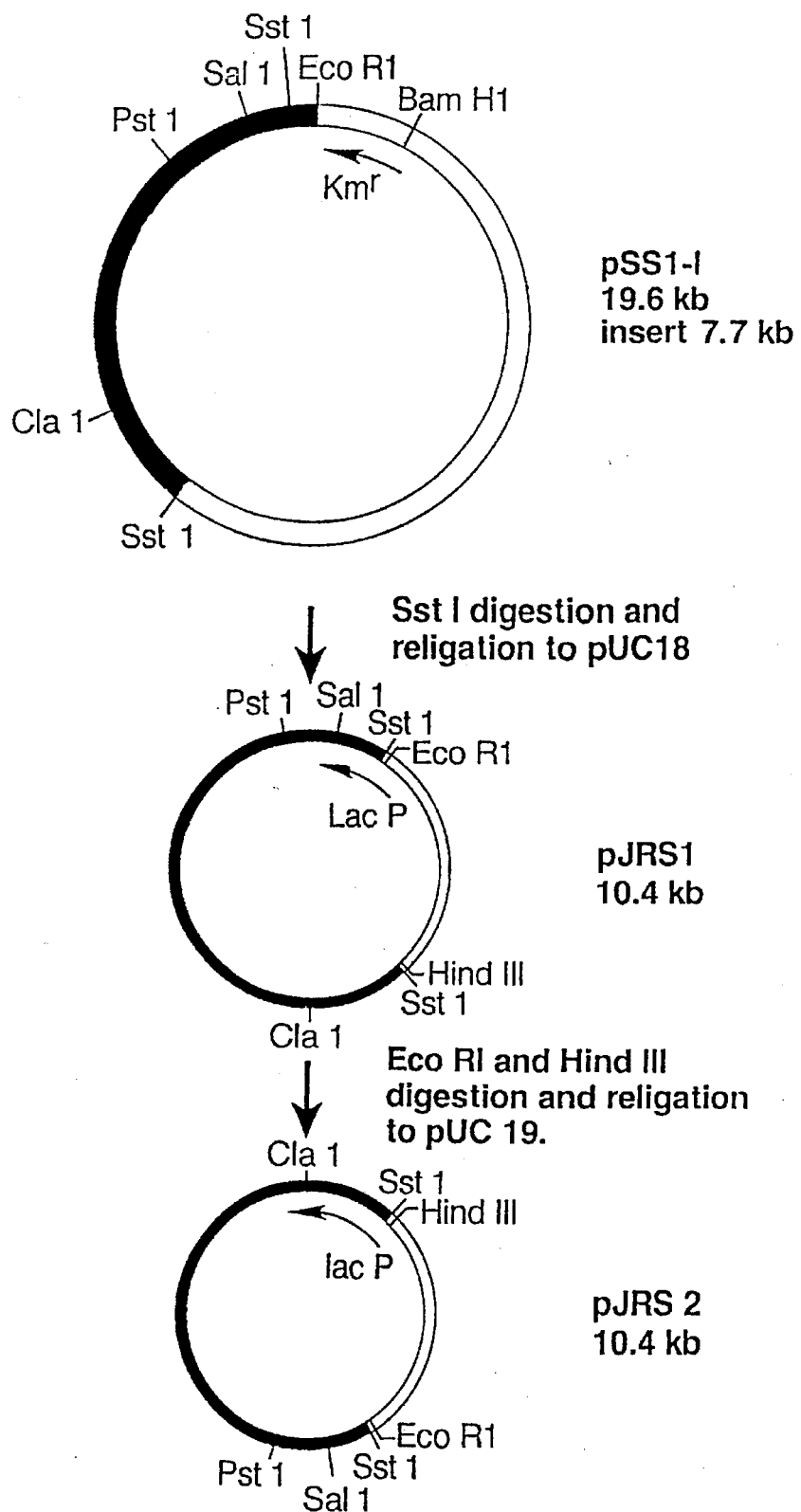
FIG. 3 shows the subcloning protocol used to isolate pJRS1 and pJRS2 with the insert of *P. putida* DNA in opposite orientations.

Cloning strategy. The vector used in these studies was pKT230, a broad-host-range plasmid of 11.9 kb able to replicate in *P. putida* and *E. coli*. Direct selection for recombinant molecules containing structural genes for subunits of branched chain keto acid dehydrogenase was achieved by complementation of *P. putida* branched chain keto acid dehydrogenase mutants. Complementation was detected by the ability of transformed mutants to grow on valine-isoleucine agar. Directed cloning with EcoRI-SstI digests yielded colonies on L agar plus kanamycin after transformation, 50 to 60% of which were $Str^s$ as a consequence of cloning into the streptomycin site. Direct plating of the transformation mixture onto valine-isoleucine agar yielded several colonies, one of which contained a plasmid with an insert of 11 kb and complemented strains JS112, JS113, JS326, and JS287. The results suggested that the plasmid, designated pSS1, contained all the structural genes for branched chain keto acid dehydrogenase.

pSS1 was subcloned by religation of a limited SalI digest which removed a 3.3-kb segment of DNA. The resulting plasmid, pSS1-1, also complemented all branched chain keto acid dehydrogenase mutants. pSS1-1 DNA hybridized with DNA from *P. putida* and *P. aeruginosa*, but not with DNA from *E. coli*. The insert was subcloned in pUC18 and pUC19 with the objective of determining the direction of transcription. The resulting plasmids were named pJRS1 and pJRS2, respectively (FIG. 3).

Stability of pSS1-1 in *P. putida*. The stability of pSS1-1 in *P. putida* was determined by subculturing in L broth with or without kanamycin. All colonies of *P. putida* JS287 (pKT230) were $Kan^r$ after 11 serial transfers, showing that pKT230 was fully retained. However, strain JS287(pSS1-1) maintained the plasmid for three serial transfers after which kanamycin-sensitive, valine-isoleucine-negative colonies appeared, and by the eleventh transfer, only 3% of the colonies were kanamycin positive.

Expression of structural genes of pSS1-1 in *P. putida* mutants. Several pieces of data led to the conclusion that pSS1-1 contained structural genes for all subunits of branched chain keto acid dehydrogenase. The presence of pSS1-1 resulted in production of branched chain keto acid dehydrogenase activity in mutants lacking E1 (Sequence ID No. 2 and No. 3) (JS113); E1, E2, and LPD-Val (Sequences ID Nos. 2, 3, 4, and 5) (JS326); and LPD-Val (JS287) (Table 5).

TABLE 5

Branched chain keto acid dehydrogenase activities of
P. putida mutants transformed with pSS1-1

| Strain | Plasmid | Sp act of branched chain keto acid dehydrogenase[a] |
|---|---|---|
| JS113 | pKT230 | 0 |
| JS113 | pSS1-1 | 142 |
| JS326 | pKT230 | 1 |
| JS236 | pSS1-1 | 94 |
| JS287 | pKT230 | 4 |
| JS287 | pSS1-1 | 160 |

[a]The specific activity of branched chain keto acid dehydrogenase is nanomoles of NAD reduced per minute per milligram of protein. Cultures were grown in GASV medium.

For comparison, the specific activities of P. putida PpG2 (pKT230) and P. putida PpG2(pSS1-1) grown in valine-isoleucine medium were 54 and 314 nmol of NADH produced per min per mg of protein, respectively. P. putida mutants transformed with pKT230 did not regain branched chain keto acid dehydrogenase activity. The presence of all three subunits of branched chain keto acid dehydrogenase was demonstrated in mutants of P. putida (pSS1-1) by enzyme assays for E1 (Sequence ID Nos. 2 and 3) and E2 (Sequence ID No. 4) and by precipitation of LPD-Val (Sequence ID No. 5) with specific antisera. When the complex was purified from P. putida JS112(pSS1-1) it contained four polypeptides with the same molecular weights as complex purified from the wild type.

Regulation of branched chain keto acid dehydrogenase formation. Branched chain keto acid dehydrogenase activity was regulated by limitation of ammonium ion and by catabolite repression in P. putida PpG2 (Table 6).

TABLE 6

Nitrogen control of branched chain keto acid dehydrogenase synthesis

| Additions to valine-isoleucine medium | | | Sp act of branched chain keto acid dehydrogenase[a] |
|---|---|---|---|
| 40 mM NH$_4$ | 20 mM glucose | 30 mM succinate | |
| *P. putida* | | | |
| PpG2 | | | |
| + | − | − | 53 |
| − | − | − | 65 |
| + | + | − | 12 |
| − | + | − | 34 |
| + | − | + | 20 |
| − | − | + | 31 |
| *P. putida* | | | |
| JS112 (pSS1-1) | | | |
| + | − | − | 234 |
| − | − | − | 206 |
| + | + | − | 202 |
| − | + | − | 151 |
| + | − | + | 266 |
| − | − | + | 265 |

[a]The specific activity of branched chain keto acid dehydrogenase is nanomoles of NAD reduced per minute per milligram of protein. Cultures were grown in GASV medium.

Valine-isoleucine medium, which contained 40 mM ammonium ion, was used to obtain the data in Table 6. Where indicated, ammonium ion was deleted from the salt solution, leaving valine and isoleucine as the nitrogen sources. The presence of ammonium ion repressed complex formation, in particular, when supplemented with glucose. This is the typical situation for metabolism of N-containing compounds by gram-negative bacteria. Glucose and succinate also repressed branched chain keto acid dehydrogenase formation compared with that of control cells grown on valine-isoleucine medium. In contrast, neither the source of nitrogen nor the presence of glucose or succinate had any effect on complex formation by P. putida JS112(pSS1-1) which produced branched chain keto acid dehydrogenase constitutively. All other mutants of P. putida transformed with pSS1-1 also produced branched chain keto acid dehydrogenase constitutively.

Expression of branched chain keto acid dehydrogenase in E. coli. E. coli does not grow in media containing branched chain amino acids as the carbon sources. Therefore, production of branched chain keto acid dehydrogenase by E. coli carrying pSS1-1 would be evidence that structural genes had been cloned. E. coli HB101 was transformed with pKT230 and pSS1-1 and grown in GAS and GASV media, and cell extracts were examined for branched chain keto acid dehydrogenase. Surprisingly, the data in Table 7 show that E. coli HB101(pSS1-1) produced higher amounts of branched chain keto acid dehydrogenase in media containing valine.

TABLE 7

Expression of PSS1-1 structural genes in E. coli HB101

| | | Sp act | |
|---|---|---|---|
| Plasmid | Medium | E1[a] | Branched chain keto acid dehydrogenase[b] |
| pKT230 | GAS | 0.0 | 0 |
| pKT230 | GASV | 0.4 | 0 |
| pSS1-1 | GAS | 7.7 | 7 |
| pSS1-1 | GASV | 20 | 48 |

[a]The specific activity is nanomoles of carbon dioxide released per 15 min per miligram of protein.
[b]The specific activity of branched chain keto acid dehydrogenase is nanomoles of NAD reduced per minute per milligram of protein. Cultures were grown in GASV medium.

This is also reflected in the specific activity of the E1 subunit (Sequence ID Nos. 2 and 3) which was nearly three times higher when HB101(pSS1-1) was grown in GASV medium compared with growth in GAS medium. It was not possible to measure E2 (Sequence ID No. 4) activity since E. coli contains a deacylase which gave a high endogenous rate with isobutyryl coenzyme A.

The data in Table 8 reinforce this result and show that relatively high amounts of L-valine are needed for induction of branched chain keto acid dehdrogenase in HB101(pSS1-1), while P. putida JS287(pSS1-1) produced branched chain keto acid dehydrogenase constitutively.

TABLE 8

Induction of branched chain keto acid dehydrogenase in *E. coli* HB101(pSS1-1)

| Concn of L-valine in medium (mM) | Sp act of branched chain keto acid dehydrogenase[a] in: | |
|---|---|---|
| | *E. coli* HB101(pSS1-1) | *P. putida* JS287(pss1-1) |
| 0.0 | 12 | 300 |
| 0.1 | 14 | 296 |
| 0.5 | 11 | 325 |
| 2.0 | 7 | 264 |
| 10.0 | 38 | 231 |
| 25.0 | 112 | 234 |

[a]The specific activity of branched chain keto acid dehydrogenase is nanomoles of NAD reduced per minute per milligram of protein. Cultures were grown in GASV medium.

Extracts of *E. coli* HB101(pSS1-1) required coenzyme A for branched chain keto acid dehydrogenase activity and were slightly dependent on thiamine $PP_i$ and L-valine, although the latter dependence is difficult to demonstrate in cell extracts.

Expression in minicells. To demonstrate the production of branched chain keto acid dehydrogenase subunits, we transformed a minicell-producing strain, *E. coli* $_x$925, was transformed with pKT230 and pSS1-1. The minicells carrying pSS1-1 produced three radioactive peptides with molecular weights in sodium dodecyl sulfate-polyacrylamide gel electrophoresis of 39,000, 45,000, and 53,000 compared with molecular weights of 37,000, 39,000, 46,000, and 49,000 for the purified complex. Enzyme assays of cell extracts of *E. coli* $_x$925(pSS1-1) verified that branched chain keto acid dehydrogenase activity was present.

Expression of branched chain keto acid dehydrogenase from pJRS1 and pJRS2 templates. To resolve the problem of expression of branched chain keto acid dehydrogenase structural genes from pSS1-1 in minicells, *E. coli* JM109 was transformed with pJRS1 and pJRS2 which contained the insert of *P. putida* DNA in opposite orientations. *E. coli* JM109(pJRS1) produced large amounts of E1 (Sequence ID No. 2 and 3) and of branched chain keto acid dehydrogenase (Table 9).

TABLE 9

Expression of structural genes of pJRS1 and pJRS2 in *E. coli* JM109

| plasmid | Addition to 2 × YT medium (mM) | Sp Act | | |
|---|---|---|---|---|
| | | E1[a] | Lipoamide dehydrogenase[b] | Branched chain keto acid dehydrogenase[c] |
| puC18 | None | 1.5 | 190 | 0.0 |
| | Glucose (10) | ND[d] | 170 | 0.0 |
| | IPTG[e] (0.15) | 1.5 | 120 | 0.0 |
| pJRS1 | None | 141 | 1,700 | 130 |
| | Glucose (10) | 82 | 800 | 110 |
| | IPTG (0.15) | 191 | 1,800 | 150 |
| pJRS2 | None | 6.4 | 310 | 0.0 |
| | Glucose (10) | ND | 180 | 0.0 |
| | IPTG (0.15) | 4.0 | 400 | 0.6 |

[a]The specific activity of branched chain keto acid dehydrogenase is nanomoles of NAD reduced per minute per milligram of protein. Cultures were grown in GASV medium.
[b]The specific activity is nanomoles of NADH oxidized per minute per milligram of protein.
[c]The specific activity of branched chain keto acid dehydrogenase is nanomoles of NAD reduced per minute per milligram of protein. Cultures were grown in GASV medium.
[d]ND, Not determined.
[e]IPTG, Isopropyl-β-D-thiogalactopyranoside.

The formation of LPD-Val (Sequence ID No. 5) was demonstrated directly by the use of specific antiserum and indirectly by the greatly increased activity of lipoamide dehydrogenase in extracts of *E. coli* JM109(pJRS1). In contrast, *E. coli* JM109(pJRS2) produced negligible amounts of branched chain keto acid dehydrogenase (Table 9). The expression of branched chain keto acid dehydrogenase is clearly constitutive in *E. coli* JM109(pJRS1), although glucose had a slight repressive effect and isopropyl-β-D-thiogalactopyranoside appeared to have a slight inductive effect. However, failure of *E. coli* JM109 (pJRS2) to produce significant amounts of branched chain keto acid dehydrogenase indicated that it was the pUC promoter which was read by *E. coli* RNA polymerase.

pUC18, pJRS1, and pJRS2 were used as DNA templates in the in vitro procaryotic translation system to determine the size and number of transcripts on the *P. putida* DNA. With pJRS1 as the template, four polypeptides were produced with molecular weights of 37,000, 39,000, 47,000, and 49,000 which were superimposable on those from a purified preparation of branched chain keto acid dehydrogenase included as a control. When pJRS2 was the template, trace amounts of these same four polypeptides were produced, suggesting that Pseudomonas promoters were being read by *E. coli* RNA polymerase, although rather inefficiently. In this same experiment, pKT230, pSS1, and pSS1-1 were also used as DNA templates, but no radioactive proteins were formed other than those associated with pKT230.

Figure 4:
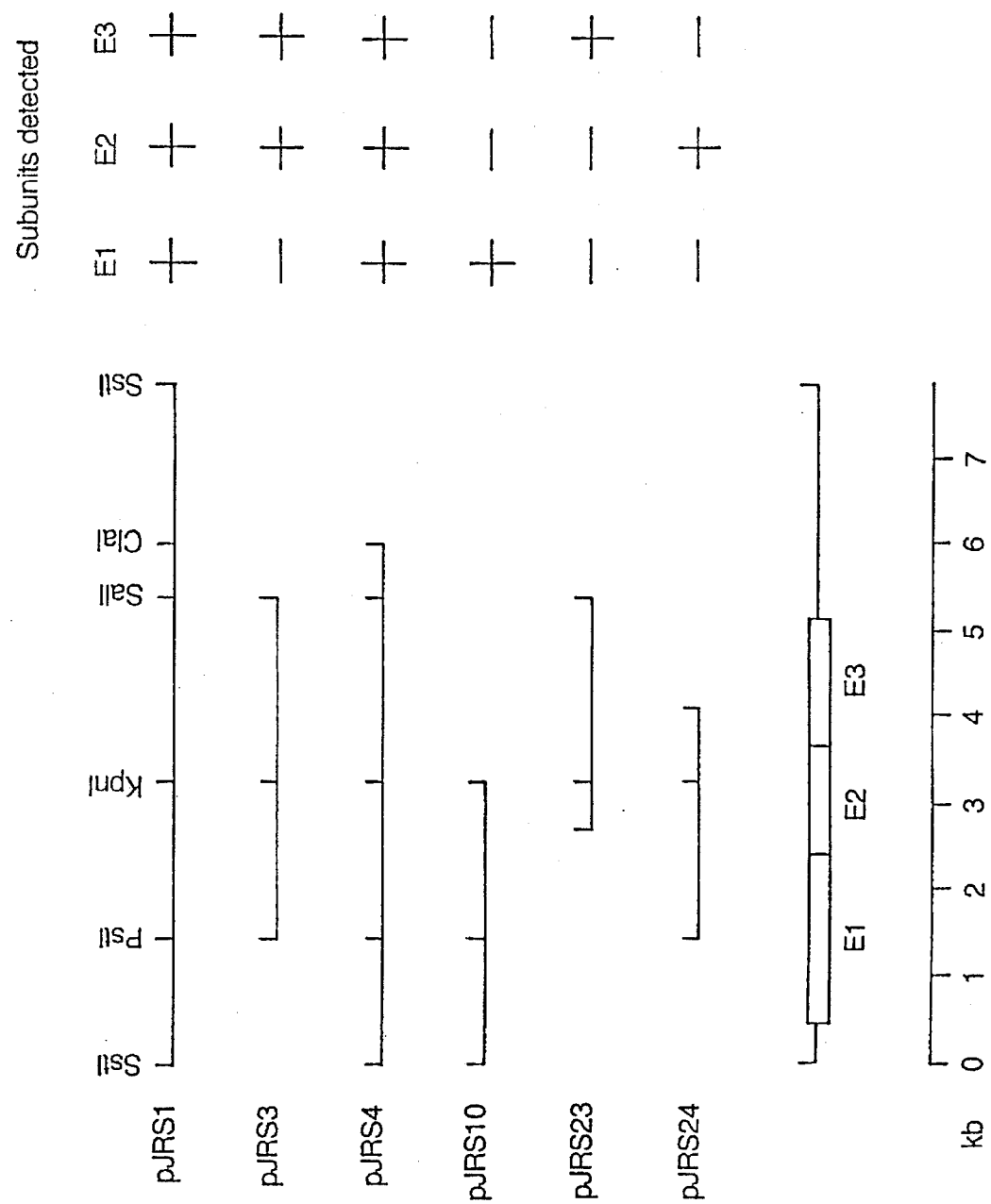
FIG. 4 shows the restriction maps of plasmids which contain structural genes for branched chain keto acid dehydrogenase THe N-terminal coding region is at the left, and the transcription is from left to right for all structural genes.

Location of structural genes. The location and order of structural genes for branched chain keto acid dehydrogenase were established by subcloning into pUC18 or pUC19 and identifying the gene products by the methods described below (FIG. 4). The N-terminal coding region of each gene is shown at the left of FIG. 4. The smallest fragment which contained all the structural genes was pJRS4, which is 6 kp in length. Extracts of *E. coli* TB1(pJRS4) contained branched chain keto acid dehydrogenase, and when pJRS4 was used as the DNA template in the transcription-translation system, four protein bands with the correct molecular weights were produced. pJRS10 contains the structural genes for the E1 subunit(s) (Sequence ID Nos. 2 and 3). Proteins with molecular weights of 37,000 and 39,000 were produced when pJRS10 was the template in the transcription-translation system. Also, extracts of *E. coli* TB1(pJRS10) supplemented the heat-treated Sepharose CL4B fraction which contains active E2 and E3 subunits (Sequence ID Nos. 4 and 5 respectively), producing active branched chain keto acid dehydrogenase. pJRS23 contains the complete structural gene for LPD-Val (Sequence ID No. 5) which was established by showing that extracts of *E. coli* TB1(pJRS23) reacted with specific anti-LPD-Val serum and complemented extracts of *P. putida* JS287. pJRS24 contained only the structural genes for the E2 subunit (Sequence ID No. 4) since extracts of *E. coli* TB1(pJRS10) and purified LPD-Val yielded active branched chain keto acid dehydrogenase. No activity was obtained when extracts of *E. coli* TB1(pJRS10) and *E. coli* TB1(pJRS24) were mixed unless purified LPD-Val was added, showing that pJRS24 did not contain the structural gene for LPD-Val (Sequence ID No. 5).

EXAMPLE 3

An example of how to express foreign genes in *Pseudomonas putida* using the bkad promoter (Sequence ID No. 6) is to start with plasmid pJRS55 (ATCC #68403). In order to insert a gene, pJRS55 could be digested with SacI and the 11 kb fragment containing the promoter (Sequence ID No. 6) and leader isolated. The sticky ends could be blunted with Klenow Regent and deoxynucleoside triphosphates. This provides a restriction site behind the promoter (Sequence ID No. 6) and leader which can be used with any blunt-ended DNA fragment.

As an example of a gene that could be inserted, lpdV of *P. putida* could be removed from plasmid pJRS54 (ATCC #68405) by digestion with ScaI. This digest would release the entire lpdV gene (Sequence ID No. 5) in a blunt-ended fragment which can be ligated to the 11 kb promoter-leader fragment. This would provide a mixture of the desired plasmid plus a construct with the lpdV gene (Sequence ID No. 5) in the opposite orientation to the bkad promoter (Sequence ID No. 6). The ligation mixture could be used to transform *P. putida* which is placated on L-agar plus ampicillin. The correct construct could be identified by picking several colonies, isolating the plasmid and digesting it with several restriction enzymes in order to determine the orientation of the insert.

All patent applications and publications cited herein are hereby incorporated by reference into the present application.

Changes may be made in the embodiments of the invention described herein or in parts or elements of the embodiments described herein or in the steps or in the sequence of steps of the methods described herein without departing from the spirit and scope of the invention as defined in the following claims.

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
        ( A ) LENGTH: 6122 base pairs
        ( B ) TYPE: Nucleic acid
        ( C ) STRANDEDNESS: Double stranded
        ( D ) TOPOLOGY: Circular ( i i ) MOLECULE TYPE: Genomic DNA
        ( A ) DESCRIPTION: Seq ID No 1 is genomic DNA from P. putida
            strain PpG2 which contains the control region regulating
            expression of the bkd operon and the four structural genes
            of the bkd operon, bkdA1, bkdA2, bkdB and lpdV.

( i i i ) HYPOTHETICAL: No ( i v ) ANTI-SENSE: No ( v ) FRAGMENT TYPE: Not applicable ( v i ) ORIGINAL SOURCE:
        ( A ) ORGANISM: Pseudomonas putida
        ( B ) STRAIN: PpG2
        ( C ) INDIVIDUAL ISOLATE: Not applicable
        ( D ) DEVELOPMENTAL STAGE: Not applicable
        ( E ) HAPLOTYPE: Not applicable
        ( F ) TISSUE TYPE: Not applicable
        ( G ) CELL TYPE: Gram negative, aerobic bacilli
        ( H ) CELL LINE: Not applicable
        ( I ) ORGANELLE: Not applicable ( v i i ) IMMEDIATE SOURCE:
        ( A ) LIBRARY: Genomic DNA from Pseudomonas putida
        ( B ) CLONE: pJRS54

( v i i i ) POSITION IN GENOME:
        ( A ) CHROMOSOME/SEGMENT:
        ( B ) MAP POSITION: 35 Minutes (C) UNITS:

(ix) FEATURE:
    (A) NAME/KEY: Promoter plus leader
    (B) LOCATION: 1-792
    (C) IDENTIFICATION METHOD: By experiment
    (D) OTHER INFORMATION: The promoter plus leader are
        responsible for expression of the bkd operon in
        Pseudomonas putida (ix) FEATURE:
    (A) NAME/KEY: bkdA1, Gene encoding branched-chain keto acid
        dehydrogenase- decarboxylase E1 alpha subunit.
    (B) LOCATION: 805-2031. Initiating methionine codon is at
        position 802, however mature peptide does not contain N-
        terminal methionine.
    (C) IDENTIFICATION METHOD: By experiment
    (D) OTHER INFORMATION: The E1 component of branched chain keto
        acid dehydrogenase catalyzes the oxidative decarboxylation
        of the keto acid substrate. E1 is composed of two
        subunits, E1 alpha and E1 beta.

(ix) FEATURE:
    (A) NAME/KEY: bkdA2, Gene encoding branched-chain keto acid
        dehydrogenase- decarboxylase E1 beta subunit.
    (B) LOCATION: 2078-3091. Initiating methionine codon is
        position 2075, however mature peptide does not contain
        N-terminal methionine.
    (C) IDENTIFICATION METHOD: By experiment
    (D) OTHER INFORMATION: See description for Feature 2 above.

(ix) FEATURE:
    (A) NAME/KEY: bkdB Gene encoding the E2 component of branched
        chain keto acid dehydrogenase
    (B) LOCATION: 3098-4363 Initiating methionine codon is
        position 3095, however mature peptide does not contain
        N-terminal methionine.
    (C) IDENTIFICATION METHOD: By experiment
    (D) OTHER INFORMATION: E2 catalyzes the transacylation of the
        fatty acyl group from the lipoyl residue of E2 to coenzyme
        A. E2 is the core of the complex and binds E1 and E3
        components.

(ix) FEATURE:
    (A) NAME/KEY: lpdV, Gene encoding the E3 component of branched
        chain keto acid dehydrogenase.
    (B) LOCATION: 4369-5745. N-terminal methionine is present on
        mature peptide.
    (C) IDENTIFICATION METHOD: By experiment
    (D) OTHER INFORMATION: E3 is LPD- val, the specific lipoamide
        dehydrogenase which catalyzes oxidation of the
        dihydrolipoyl residue of the E2 component of branched
        chain keto acid dehydrogenase and the reduction of NAD+.

(x) PUBLICATION INFORMATION:
    (A) AUTHORS: Sokatch, John R.
        McCully, Vicki
        Gebrosky, Janet
        Sokatch, David,J.
    (B) TITLE: Isolation of a specific lipoamide dehydrogenase
        for a branched-chain keto acid dehydrogenase
        from Pseudomonas putida
    (C) JOURNAL: Journal of Bacteriology
    (D) VOLUME: 148
    (E) ISSUE:
    (F) PAGES: 639-646
    (G) DATE: 1981
    (A) AUTHORS: Sokatch,John R.
        McCully, Vicki
        Roberts, C.M.
    (B) TITLE: Purification of a branched-chain keto acid
        dehydrogenase from Pseudomonas putida
    (C) JOURNAL: Journal of Bacteriology
    (D) VOLUME: 148
    (E) ISSUE:
    (F) PAGES: 647-652
    (G) DATE: 1981
    (A) AUTHORS: Sykes, Pamela
        Burns, Gayle
        Menard, Joan Hatter, Kenneth
Sokatch, John R.
(B) TITLE: Molecular cloning of genes encoding branched-chain
keto acid dehydrogenase of Pseudomonas putida
(C) JOURNAL: Journal of Bacteriology
(D) VOLUME: 169
(E) ISSUE:
(F) PAGES: 1619-1625
(G) DATE: 1987
(A) AUTHORS: Burns, Gayle
Brown, Tracy
Hatter, Kenneth
Sokatch, John R.
(B) TITLE: Comparison of the amino acid sequences of the
transacylase components of branched-chain oxoacid
dehydrogenase of Pseudomonas putida, and the pyruvate and
2-oxoglutarate dehydrogenases of Escherichia coli
(C) JOURNAL: European Journal of Biochemistry
(D) VOLUME: 176
(E) ISSUE:
(F) PAGES: 165-169
(G) DATE: 1988
(A) AUTHORS: Burns, Gayle
Brown, Tracy
Hatter, Kenneth
Idriss, John M.
Sokatch, John R.
(B) TITLE: Similarity of the E1 subunits of branched-chain-
oxoacid dehydrogenase from Pseudomonas putida to the
corresponding subunits of mammalian branched-chain-
oxoacid and pyruvate dehydrogenases
(C) JOURNAL: European Journal of Biochemistry
(D) VOLUME: 176
(E) ISSUE:
(F) PAGES: 311-317
(G) DATE: 1988
(A) AUTHORS: Burns, Gayle
Brown, Tracy
Hatter, Kenneth
Sokatch, John R.
(B) TITLE: Sequence analysis of the lpdV gene for lipoamide
dehydrogenase of Pseudomonas putida
(C) JOURNAL: European Journal of Biochemistry
(D) VOLUME: 179
(E) ISSUE:
(F) PAGES: 61-69
(G) DATE: 1989
(A) AUTHORS: Madhusudhan, K.T.
Huang, G.
Burns, Gayle
Sokatch, J.R.
(B) TITLE: Transcriptional analysis of the promoter region of
the branched chain keto acid dehydrogenase operon of
Pseudomonas putida
(C) JOURNAL: Journal of Bacteriology
(D) VOLUME: 172
(E) ISSUE: October, 1990
(F) PAGES: 5655-5663
(G) DATE: 1990
(K) RELEVANT RESIDUES IN SEQ ID NO:1: FROM 1 TO 6122

(xi) SEQUENCE DESCRIPTION: SEQ ID NO:1:

```
CGATGCCCTG GAGCTGAGCG ATGCTCATGA CGCTTGTCCT TGTTGTTGTA GGCTGACAAC        60

AACATAGGCT GGGGGTGTTT AAAATATCAA GCAGCCTCTC GAACGCCTGG GGCCTCTTCT       120

ATCGCGCAAG GTCATGCCAT TGGCCGGCAA CGGCAAGGCT GTCTTGTAGC GCACCTGTTT       180

CAAGGCAAAA CTCGAGCGGA TATTCGCCAC ACCCGGCAAC CGGGTCAGGT AATCGAGAAA       240

CCGCTCCAGC GCCTGGATAC TCGGCAGCAG TACCCGCAAC AGGTAGTCCG GGTCGCCCGT       300

CATCAGGTAG CACTCCATCA CCTCGGGCCG TTCGGCAATT TCTTCCTCGA AGCGGTGCAG       360

CGACTGCTCT ACCTGTTTTT CCAGGCTGAC ATGGATGAAC ACATTCACAT CCAGCCCCAA       420

CGCCTCGGGC GACAACAAGG TCACCTGCTG GCGGATCACC CCCAGTTCTT CCATGGCCCG       480

CACCCGGTTG AAACAGGGCG TGGGCGACAG GTTGACCGAG CGTGCCAGCT CGGCGTTGGT       540
```

```
GATGCGGGCG TTTTCCTGCA GGCTGTTGAG AATGCCGATA TCGGTACGAT CGAGTTTGCG        600

CATGAGACAA AATCACCGGT TTTTTGTGTT TATGCGGAAT GTTTATCTGC CCCGCTCGGC        660

AAAGGCAATC AACTTGAGAG AAAAATTCTC CTGCCGGACC ACTAAGATGT AGGGGACGCT        720

GACTTACCAG TCACAAGCCG GTACTCAGCG GCGGCCGCTT CAGAGCTCAC AAAAACAAAT        780

ACCCGAGCGA GCGTAAAAAG CATG AAC GAG TAC GCC CCC CTG CGT TTG              828
                          Asn Glu Tyr Ala Pro Leu Arg Leu
                                         5
```

| | | | | | | | | | | | | | | | | |
|---|---|---|---|---|---|---|---|---|---|---|---|---|---|---|---|---|
| CAT | GTG | CCC | GAG | CCC | ACC | GGC | CGG | CCA | GGC | TGC | CAG | ACC | GAT | TTT | TCC | 876 |
| His | Val | Pro | Glu | Pro | Thr | Gly | Arg | Pro | Gly | Cys | Gln | Thr | Asp | Phe | Ser | |
| | 10 | | | | 15 | | | | | 20 | | | | | | |
| TAC | CTG | CGC | CTG | AAC | GAT | GCA | GGT | CAA | GCC | CGT | AAA | CCC | CCT | GTC | GAT | 924 |
| Tyr | Leu | Arg | Leu | Asn | Asp | Ala | Gly | Gln | Ala | Arg | Lys | Pro | Pro | Val | Asp | |
| 25 | | | | | 30 | | | | | 35 | | | | | 40 | |
| GTC | GAC | GCT | GCC | GAC | ACC | GCC | GAC | CTG | TCC | TAC | AGC | CTG | GTC | CGC | GTG | 972 |
| Val | Asp | Ala | Ala | Asp | Thr | Ala | Asp | Leu | Ser | Tyr | Ser | Leu | Val | Arg | Val | |
| | | | | 45 | | | | | 50 | | | | | 55 | | |
| CTC | GAC | GAG | CAA | GGC | GAC | GCC | CAA | GGC | CCG | TGG | GCT | GAA | GAC | ATC | GAC | 1020 |
| Leu | Asp | Glu | Gln | Gly | Asp | Ala | Gln | Gly | Pro | Trp | Ala | Glu | Asp | Ile | Asp | |
| | | | 60 | | | | | 65 | | | | | 70 | | | |
| CCG | CAG | ATC | CTG | CGC | CAA | GGC | ATG | CGC | GCC | ATG | CTC | AAG | ACG | CGG | ATC | 1068 |
| Pro | Gln | Ile | Leu | Arg | Gln | Gly | Met | Arg | Ala | Met | Leu | Lys | Thr | Arg | Ile | |
| | | 75 | | | | | 80 | | | | | 85 | | | | |
| TTC | GAC | AGC | CGC | ATG | GTG | GTT | GCC | CAG | CGC | CAG | AAG | AAG | ATG | TCC | TTC | 1116 |
| Phe | Asp | Ser | Arg | Met | Val | Val | Ala | Gln | Arg | Gln | Lys | Lys | Met | Ser | Phe | |
| | 90 | | | | | 95 | | | | | 100 | | | | | |
| TAC | ATG | CAG | AGC | CTG | GGC | GAA | GAA | GCC | ATC | GGC | AGC | GGC | CAG | GCG | CTG | 1164 |
| Tyr | Met | Gln | Ser | Leu | Gly | Glu | Glu | Ala | Ile | Gly | Ser | Gly | Gln | Ala | Leu | |
| 105 | | | | | 110 | | | | | 115 | | | | | 120 | |
| GCG | CTT | AAC | CGC | ACC | GAC | ATG | TGC | TTC | CCC | ACC | TAC | CGT | CAG | CAA | AGC | 1212 |
| Ala | Leu | Asn | Arg | Thr | Asp | Met | Cys | Phe | Pro | Thr | Tyr | Arg | Gln | Gln | Ser | |
| | | | | 125 | | | | | 130 | | | | | 135 | | |
| ATC | CTG | ATG | GCC | CGC | GAC | GTG | TCG | CTG | GTG | GAG | ATG | ATC | TGC | CAG | TTG | 1260 |
| Ile | Leu | Met | Ala | Arg | Asp | Val | Ser | Leu | Val | Glu | Met | Ile | Cys | Gln | Leu | |
| | | | 140 | | | | | 145 | | | | | 150 | | | |
| CTG | TCC | AAC | GAA | CGC | GAC | CCC | CTC | AAG | GGC | CGC | CAG | CTG | CCG | ATC | ATG | 1308 |
| Leu | Ser | Asn | Glu | Arg | Asp | Pro | Leu | Lys | Gly | Arg | Gln | Leu | Pro | Ile | Met | |
| | | 155 | | | | | 160 | | | | | 165 | | | | |
| TAC | TCG | GTA | CGC | GAG | GCC | GGC | TTC | TTC | ACC | ATC | AGC | GGC | AAC | CTG | GCG | 1356 |
| Tyr | Ser | Val | Arg | Glu | Ala | Gly | Phe | Phe | Thr | Ile | Ser | Gly | Asn | Leu | Ala | |
| | 170 | | | | | 175 | | | | | 180 | | | | | |
| ACC | CAG | TTC | GTG | CAG | GCG | GTC | GGC | TGG | GCC | ATG | GCC | TCG | GCG | ATC | AAG | 1404 |
| Thr | Gln | Phe | Val | Gln | Ala | Val | Gly | Trp | Ala | Met | Ala | Ser | Ala | Ile | Lys | |
| 185 | | | | | 190 | | | | | 195 | | | | | 200 | |
| GGC | GAT | ACC | AAG | ATT | GCC | TCG | GCC | TGG | ATC | GGC | GAC | GGC | GCC | ACT | GCC | 1452 |
| Gly | Asp | Thr | Lys | Ile | Ala | Ser | Ala | Trp | Ile | Gly | Asp | Gly | Ala | Thr | Ala | |
| | | | | 205 | | | | | 210 | | | | | 215 | | |
| GAA | TCG | GAC | TTC | CAC | ACC | GCC | CTC | ACC | TTT | GCC | CAC | GTT | TAC | CGC | GCC | 1500 |
| Glu | Ser | Asp | Phe | His | Thr | Ala | Leu | Thr | Phe | Ala | His | Val | Tyr | Arg | Ala | |
| | | | 220 | | | | | 225 | | | | | 230 | | | |
| CCG | GTG | ATC | CTC | AAC | GTG | GTC | AAC | AAC | CAG | TGG | GCC | ATC | TCA | ACC | TTC | 1548 |
| Pro | Val | Ile | Leu | Asn | Val | Val | Asn | Asn | Gln | Trp | Ala | Ile | Ser | Thr | Phe | |
| | | 235 | | | | | 240 | | | | | 245 | | | | |
| CAG | GCC | ATC | GCC | GGT | GGC | GAG | TCG | ACC | ACC | TTC | GCC | GGC | CGT | GGC | GTG | 1596 |
| Gln | Ala | Ile | Ala | Gly | Gly | Glu | Ser | Thr | Thr | Phe | Ala | Gly | Arg | Gly | Val | |
| | 250 | | | | | 255 | | | | | 260 | | | | | |
| GGC | TGC | GGC | ATC | GCT | TCG | CTG | CGG | GTG | GAC | GGC | AAC | GAC | TTC | GTC | GCC | 1644 |
| Gly | Cys | Gly | Ile | Ala | Ser | Leu | Arg | Val | Asp | Gly | Asn | Asp | Phe | Val | Ala | |
| 265 | | | | 270 | | | | | 275 | | | | | 280 | | |

| | |
|---|---|
| GTT TAC GCC GCT TCG CGC TGG GCT GCC GAA CGT GCC CGC CGT GGT TTG<br>Val Tyr Ala Ala Ser Arg Trp Ala Ala Glu Arg Ala Arg Arg Gly Leu<br>285 290 295 | 1692 |
| GGC CCG AGC CTG ATC GAG TGG GTC ACC TAC CGT GCC GGC CCG CAC TCG<br>Gly Pro Ser Leu Ile Glu Trp Val Thr Tyr Arg Ala Gly Pro His Ser<br>300 305 310 | 1740 |
| ACC TCG GAC GAC CCG TCC AAG TAC CGC CCT GCC GAT GAC TGG AGC CAC<br>Thr Ser Asp Asp Pro Ser Lys Tyr Arg Pro Ala Asp Asp Trp Ser His<br>315 320 325 | 1788 |
| TTC CCG CTG GGT GAC CCG ATC GCC CGC CTG AAG CAG CAC CTG ATC AAG<br>Phe Pro Leu Gly Asp Pro Ile Ala Arg Leu Lys Gln His Leu Ile Lys<br>330 335 340 | 1836 |
| ATC GGC CAC TGG TGC GAA GAA GAA CAC CAG GCC ACC ACG GCC GAG TTC<br>Ile Gly His Trp Cys Glu Glu Glu His Gln Ala Thr Thr Ala Glu Phe<br>345 350 355 360 | 1884 |
| GAA GCG GCC GTG ATT GCT GCG CAA AAA GAA GCC GAG CAG TAC GGC ACC<br>Glu Ala Ala Val Ile Ala Ala Gln Lys Glu Ala Glu Gln Tyr Gly Thr<br>365 370 375 | 1932 |
| CTG GCC AAC GGT CAC ATC CCG AGC GCC GCC TCG ATG TTC GAG GAC GTG<br>Leu Ala Asn Gly His Ile Pro Ser Ala Ala Ser Met Phe Glu Asp Val<br>380 385 390 | 1980 |
| TAC AAG GAG ATG CCC GAC CAC CTG CGC CGC CAA CGC CAG GAA CTG GGG<br>Tyr Lys Glu Met Pro Asp His Leu Arg Arg Gln Arg Gln Glu Leu Gly<br>395 400 405 | 2028 |
| GTT TGAGATGAAC GACCACAACA ACAGCATCAA CCCGGAAACC GCCATG GCC ACC<br>Val Ala Thr | 2083 |
| ACT ACC ATG ACC ATG ATC CAG GCC CTG CGC TCG GCC ATG GAT GTC ATG<br>Thr Thr Met Thr Met Ile Gln Ala Leu Arg Ser Ala Met Asp Val Met<br>5 10 15 | 2131 |
| CTT GAG CGC GAC GAC AAT GTG GTG GTG TAC GGC CAG GAC GTC GGC TAC<br>Leu Glu Arg Asp Asp Asn Val Val Val Tyr Gly Gln Asp Val Gly Tyr<br>20 25 30 | 2179 |
| TTC GGC GGC GTG TTC CGC TGC ACC GAA GGC CTG CAG ACC AAG TAC GGC<br>Phe Gly Gly Val Phe Arg Cys Thr Glu Gly Leu Gln Thr Lys Tyr Gly<br>35 40 45 50 | 2227 |
| AAG TCC CGC GTG TTC GAC GCG CCC ATC TCT GAA AGC GGC ATC GTC GGC<br>Lys Ser Arg Val Phe Asp Ala Pro Ile Ser Glu Ser Gly Ile Val Gly<br>55 60 65 | 2275 |
| ACC GCC GTG GGC ATG GGT GCC TAC GGC CTG CGC CCG GTG GTG GAA ATC<br>Thr Ala Val Gly Met Gly Ala Tyr Gly Leu Arg Pro Val Val Glu Ile<br>70 75 80 | 2323 |
| CAG TTC GCT GAC TAC TTC TAC CCG GCC TCC GAC CAG ATC GTT TCT GAA<br>Gln Phe Ala Asp Tyr Phe Tyr Pro Ala Ser Asp Gln Ile Val Ser Glu<br>85 90 95 | 2371 |
| ATG GCC CGC CTG CGC TAC CGT TCG GCC GGC GAG TTC ATC GCC CCG CTG<br>Met Ala Arg Leu Arg Tyr Arg Ser Ala Gly Glu Phe Ile Ala Pro Leu<br>100 105 110 | 2419 |
| ACC CTG CGT ATG CCC TGC GGT GGC GGT ATC TAT GGC GGC CAG ACA CAC<br>Thr Leu Arg Met Pro Cys Gly Gly Gly Ile Tyr Gly Gly Gln Thr His<br>115 120 125 130 | 2467 |
| AGC CAG AGC CCG GAA GCG ATG TTC ACT CAG GTG TGC GGC CTG CGC ACC<br>Ser Gln Ser Pro Glu Ala Met Phe Thr Gln Val Cys Gly Leu Arg Thr<br>135 140 145 | 2515 |
| GTA ATG CCA TCC AAC CCG TAC GAC GCC AAA GGC CTG CTG ATT GCC TCG<br>Val Met Pro Ser Asn Pro Tyr Asp Ala Lys Gly Leu Leu Ile Ala Ser<br>150 155 160 | 2563 |
| ATC GAA TGC GAC GAC CCG GTG ATC TTC CTG GAG CCC AAG CGC CTG TAC<br>Ile Glu Cys Asp Asp Pro Val Ile Phe Leu Glu Pro Lys Arg Leu Tyr<br>165 170 175 | 2611 |

| | | | | | | | | | | | | | | | | |
|---|---|---|---|---|---|---|---|---|---|---|---|---|---|---|---|---|
| AAC | GGC | CCG | TTC | GAC | GGC | CAC | CAT | GAC | CGC | CCG | GTT | ACG | CCG | TGG | TCG | 2659 |
| Asn | Gly | Pro | Phe | Asp | Gly | His | His | Asp | Arg | Pro | Val | Thr | Pro | Trp | Ser | |
| | 180 | | | | 185 | | | | | 190 | | | | | | |
| AAA | CAC | CCG | CAC | AGC | GCC | GTG | CCC | GAT | GGC | TAC | TAC | ACC | GTG | CCA | CTG | 2707 |
| Lys | His | Pro | His | Ser | Ala | Val | Pro | Asp | Gly | Tyr | Tyr | Thr | Val | Pro | Leu | |
| 195 | | | | | 200 | | | | | 205 | | | | | 210 | |
| GAC | AAG | GCC | GCC | ATC | ACC | CGC | CCC | GGC | AAT | GAC | GTG | AGC | GTG | CTC | ACC | 2755 |
| Asp | Lys | Ala | Ala | Ile | Thr | Arg | Pro | Gly | Asn | Asp | Val | Ser | Val | Leu | Thr | |
| | | | | 215 | | | | | 220 | | | | | 225 | | |
| TAT | GGC | ACC | ACC | GTG | TAC | GTG | GCC | CAG | GTG | GCC | GCC | GAA | GAA | AGT | GGC | 2803 |
| Tyr | Gly | Thr | Thr | Val | Tyr | Val | Ala | Gln | Val | Ala | Ala | Glu | Glu | Ser | Gly | |
| | | | 230 | | | | | 235 | | | | | 240 | | | |
| GTG | GAT | GCC | GAA | GTG | ATC | GAC | CTG | CGC | AGC | CTG | TGG | CCG | CTA | GAC | CTG | 2851 |
| Val | Asp | Ala | Glu | Val | Ile | Asp | Leu | Arg | Ser | Leu | Trp | Pro | Leu | Asp | Leu | |
| | | | 245 | | | | | 250 | | | | | 255 | | | |
| GAC | ACC | ATC | GTC | GAG | TCG | GTG | AAA | AAG | ACC | GGC | CGT | TGC | GTG | GTA | GTA | 2899 |
| Asp | Thr | Ile | Val | Glu | Ser | Val | Lys | Lys | Thr | Gly | Arg | Cys | Val | Val | Val | |
| | | 260 | | | | | 265 | | | | | 270 | | | | |
| CAC | GAG | GCC | ACC | CGT | ACT | TGT | GGC | TTT | GGC | GCA | GAA | CTG | GTG | TCG | CTG | 2947 |
| His | Glu | Ala | Thr | Arg | Thr | Cys | Gly | Phe | Gly | Ala | Glu | Leu | Val | Ser | Leu | |
| 275 | | | | | 280 | | | | | 285 | | | | | 290 | |
| GTG | CAG | GAG | CAC | TGC | TTC | CAC | CAC | CTG | GAG | GCG | CCG | ATC | GAG | CGC | GTC | 2995 |
| Val | Gln | Glu | His | Cys | Phe | His | His | Leu | Glu | Ala | Pro | Ile | Glu | Arg | Val | |
| | | | | 295 | | | | | 300 | | | | | 305 | | |
| ACC | GGT | TGG | GAC | ACC | CCC | TAC | CCT | CAC | GCG | CAG | GAA | TGG | GCT | TAC | TTC | 3043 |
| Thr | Gly | Trp | Asp | Thr | Pro | Tyr | Pro | His | Ala | Gln | Glu | Trp | Ala | Tyr | Phe | |
| | | | 310 | | | | | 315 | | | | | 320 | | | |
| CCA | GGG | CCT | TCG | CGG | GTA | GGT | GCG | GCA | TTG | AAA | AAG | GTC | ATG | GAG | GTC | 3091 |
| Pro | Gly | Pro | Ser | Arg | Val | Gly | Ala | Ala | Leu | Lys | Lys | Val | Met | Glu | Val | |
| | | 325 | | | | | 330 | | | | | 335 | | | | |
| TGAATG | GGC | ACG | CAC | GTC | ATC | AAG | ATG | CCG | GAC | ATT | GGC | GAA | GGC | ATC | | 3139 |
| | Gly | Thr | His | Val | Ile | Lys | Met | Pro | Asp | Ile | Gly | Glu | Gly | Ile | | |
| | | | | 5 | | | | | 10 | | | | | | | |
| GCG | CAG | GTC | GAA | TTG | GTG | GAA | TGG | TTC | GTC | AAG | GTG | GGC | GAC | ATC | ATC | 3187 |
| Ala | Gln | Val | Glu | Leu | Val | Glu | Trp | Phe | Val | Lys | Val | Gly | Asp | Ile | Ile | |
| 15 | | | | | 20 | | | | | 25 | | | | | 30 | |
| GCC | GAG | GAC | CAA | GTG | GTA | GCC | GAC | GTC | ATG | ACC | GAC | AAG | GCC | ACC | GTG | 3235 |
| Ala | Glu | Asp | Gln | Val | Val | Ala | Asp | Val | Met | Thr | Asp | Lys | Ala | Thr | Val | |
| | | | | 35 | | | | | 40 | | | | | 45 | | |
| GAA | ATC | CCG | TCG | CCG | GTC | AGC | GGC | AAG | GTG | CTG | GCC | CTG | GGT | GGC | CAG | 3283 |
| Glu | Ile | Pro | Ser | Pro | Val | Ser | Gly | Lys | Val | Leu | Ala | Leu | Gly | Gly | Gln | |
| | | | 50 | | | | | 55 | | | | | 60 | | | |
| CCA | GGT | GAA | GTG | ATG | GCG | GTC | GGC | AGT | GAG | CTG | ATC | CGC | ATC | GAA | GTG | 3331 |
| Pro | Gly | Glu | Val | Met | Ala | Val | Gly | Ser | Glu | Leu | Ile | Arg | Ile | Glu | Val | |
| | | 65 | | | | | 70 | | | | | 75 | | | | |
| GAA | GGC | AGC | GGC | AAC | CAT | GTG | GAT | GTG | CCG | CAA | GCC | AAG | CCG | GCC | GAA | 3379 |
| Glu | Gly | Ser | Gly | Asn | His | Val | Asp | Val | Pro | Gln | Ala | Lys | Pro | Ala | Glu | |
| | | 80 | | | | | 85 | | | | | 90 | | | | |
| GTG | CCT | GCG | GCA | CCG | GTA | GCC | GCT | AAA | CCT | GAA | CCA | CAG | AAA | GAC | GTT | 3427 |
| Val | Pro | Ala | Ala | Pro | Val | Ala | Ala | Lys | Pro | Glu | Pro | Gln | Lys | Asp | Val | |
| 95 | | | | | 100 | | | | | 105 | | | | | 110 | |
| AAA | CCG | GCG | GCG | TAC | CAG | GCG | TCA | GCC | AGC | CAC | GAG | GCA | GCG | CCC | ATC | 3475 |
| Lys | Pro | Ala | Ala | Tyr | Gln | Ala | Ser | Ala | Ser | His | Glu | Ala | Ala | Pro | Ile | |
| | | | | 115 | | | | | 120 | | | | | 125 | | |
| GTG | CCG | CGC | CAG | CCG | GGC | GAC | AAG | CCG | CTG | GCC | TCG | CCG | GCG | GTG | CGC | 3523 |
| Val | Pro | Arg | Gln | Pro | Gly | Asp | Lys | Pro | Leu | Ala | Ser | Pro | Ala | Val | Arg | |
| | | | 130 | | | | | 135 | | | | | 140 | | | |
| AAA | CGC | GCC | CTC | GAT | GCC | GGC | ATC | GAA | TTG | CGT | TAT | GTG | CAC | GGC | AGC | 3571 |
| Lys | Arg | Ala | Leu | Asp | Ala | Gly | Ile | Glu | Leu | Arg | Tyr | Val | His | Gly | Ser | |
| | | | 145 | | | | | 150 | | | | | 155 | | | |

| | | | | | | | | | | | | | | | | |
|---|---|---|---|---|---|---|---|---|---|---|---|---|---|---|---|---|
| GGC | CCG | GCC | GGG | CGC | ATC | CTG | CAC | GAA | GAC | CTC | GAC | GCG | TTC | ATG | AGC | 3619 |
| Gly | Pro | Ala | Gly | Arg | Ile | Leu | His | Glu | Asp | Leu | Asp | Ala | Phe | Met | Ser | |
| | 160 | | | | 165 | | | | | 170 | | | | | | |
| AAA | CCG | CAA | AGC | GCT | GCC | GGG | CAA | ACC | CCC | AAT | GGC | TAT | GCC | AGG | CGC | 3667 |
| Lys | Pro | Gln | Ser | Ala | Ala | Gly | Gln | Thr | Pro | Asn | Gly | Tyr | Ala | Arg | Arg | |
| 175 | | | | | 180 | | | | | 185 | | | | | 190 | |
| ACC | GAC | AGC | GAG | CAG | GTG | CCG | GTG | ATC | GGC | CTG | CGC | CGC | AAG | ATC | GCC | 3715 |
| Thr | Asp | Ser | Glu | Gln | Val | Pro | Val | Ile | Gly | Leu | Arg | Arg | Lys | Ile | Ala | |
| | | | | 195 | | | | | 200 | | | | | 205 | | |
| CAG | CGC | ATG | CAG | GAC | GCC | AAG | CGC | CGG | GTC | GCG | CAC | TTC | AGC | TAT | GTG | 3763 |
| Gln | Arg | Met | Gln | Asp | Ala | Lys | Arg | Arg | Val | Ala | His | Phe | Ser | Tyr | Val | |
| | | | 210 | | | | | 215 | | | | | 220 | | | |
| GAA | GAA | ATC | GAC | GTC | ACC | GCC | CTG | GAA | GCC | CTG | CGC | CAG | CAG | CTC | AAC | 3811 |
| Glu | Glu | Ile | Asp | Val | Thr | Ala | Leu | Glu | Ala | Leu | Arg | Gln | Gln | Leu | Asn | |
| | | 225 | | | | | 230 | | | | | 235 | | | | |
| AGC | AAG | CAC | GGC | GAC | AGC | CGC | GGC | AAG | CTG | ACA | CTG | CTG | CCG | TTC | CTG | 3859 |
| Ser | Lys | His | Gly | Asp | Ser | Arg | Gly | Lys | Leu | Thr | Leu | Leu | Pro | Phe | Leu | |
| | 240 | | | | | 245 | | | | | 250 | | | | | |
| GTG | CGC | GCC | CTG | GTC | GTG | GCA | CTG | CGT | GAC | TTC | CCG | CAG | ATA | AAC | GCC | 3907 |
| Val | Arg | Ala | Leu | Val | Val | Ala | Leu | Arg | Asp | Phe | Pro | Gln | Ile | Asn | Ala | |
| 255 | | | | | 260 | | | | | 265 | | | | | 270 | |
| ACC | TAC | GAT | GAC | GAA | GCG | CAG | ATC | ATC | ACC | CGC | CAT | GGC | GCG | GTG | CAT | 3955 |
| Thr | Tyr | Asp | Asp | Glu | Ala | Gln | Ile | Ile | Thr | Arg | His | Gly | Ala | Val | His | |
| | | | | 275 | | | | | 280 | | | | | 285 | | |
| GTG | GGC | ATC | GCC | ACC | CAA | GGT | GAC | AAC | GGC | CTG | ATG | GTA | CCC | GTG | CTG | 4003 |
| Val | Gly | Ile | Ala | Thr | Gln | Gly | Asp | Asn | Gly | Leu | Met | Val | Pro | Val | Leu | |
| | | | 290 | | | | | 295 | | | | | 300 | | | |
| CGC | CAC | GCC | GAA | GCG | GGC | AGC | CTG | TGG | GCC | AAT | GCC | GGT | GAG | ATT | TCA | 4051 |
| Arg | His | Ala | Glu | Ala | Gly | Ser | Leu | Trp | Ala | Asn | Ala | Gly | Glu | Ile | Ser | |
| | | 305 | | | | | 310 | | | | | 315 | | | | |
| CGC | CTG | GCC | AAC | GCT | GCG | CGC | AAC | AAC | AAG | GCC | AGC | CGC | GAA | GAG | CTG | 4099 |
| Arg | Leu | Ala | Asn | Ala | Ala | Arg | Asn | Asn | Lys | Ala | Ser | Arg | Glu | Glu | Leu | |
| | 320 | | | | | 325 | | | | | 330 | | | | | |
| TCC | GGT | TCG | ACC | ATT | ACC | CTG | ACC | AGC | CTC | GGC | GCC | CTG | GGC | GGC | ATC | 4147 |
| Ser | Gly | Ser | Thr | Ile | Thr | Leu | Thr | Ser | Leu | Gly | Ala | Leu | Gly | Gly | Ile | |
| 335 | | | | | 340 | | | | | 345 | | | | | 350 | |
| GTC | AGC | ACG | CCG | GTG | GTC | AAC | ACC | CCG | GAA | GTG | GCG | ATC | GTC | GGT | GTC | 4195 |
| Val | Ser | Thr | Pro | Val | Val | Asn | Thr | Pro | Glu | Val | Ala | Ile | Val | Gly | Val | |
| | | | | 355 | | | | | 360 | | | | | 365 | | |
| AAC | CGC | ATG | GTT | GAG | CGG | CCC | GTG | GTG | ATC | GAC | GGC | CAG | ATC | GTC | GTG | 4243 |
| Asn | Arg | Met | Val | Glu | Arg | Pro | Val | Val | Ile | Asp | Gly | Gln | Ile | Val | Val | |
| | | | 370 | | | | | 375 | | | | | 380 | | | |
| CGC | AAG | ATG | ATG | AAC | CTG | TCC | AGC | TCG | TTC | GAC | CAC | CGC | GTG | GTC | GAT | 4291 |
| Arg | Lys | Met | Met | Asn | Leu | Ser | Ser | Ser | Phe | Asp | His | Arg | Val | Val | Asp | |
| | | 385 | | | | | 390 | | | | | 395 | | | | |
| GGC | ATG | GAC | GCC | GCC | CTG | TTC | ATC | CAG | GCC | GTG | CGT | GGC | CTG | CTC | GAA | 4339 |
| Gly | Met | Asp | Ala | Ala | Leu | Phe | Ile | Gln | Ala | Val | Arg | Gly | Leu | Leu | Glu | |
| | 400 | | | | | 405 | | | | | 410 | | | | | |
| CAA | CCC | GCC | TGC | CTG | TTC | GTG | GAG | TGAGC | ATG | CAA | CAG | ACT | ATC | | | 4383 |
| Gln | Pro | Ala | Cys | Leu | Phe | Val | Glu | | Met | Gln | Gln | Thr | Ile | | | |
| 415 | | | | | 420 | | | | | | | | 5 | | | |
| CAG | ACA | ACC | CTG | TTG | ATC | ATC | GGC | GGC | GGC | CCT | GGC | GGC | TAT | GTG | GCG | 4431 |
| Gln | Thr | Thr | Leu | Leu | Ile | Ile | Gly | Gly | Gly | Pro | Gly | Gly | Tyr | Val | Ala | |
| | | | | 10 | | | | | 15 | | | | | 20 | | |
| GCC | ATC | CGC | GCC | GGG | CAA | CTG | GGC | ATC | CCT | ACC | GTG | CTG | GTG | GAA | GGC | 4479 |
| Ala | Ile | Arg | Ala | Gly | Gln | Leu | Gly | Ile | Pro | Thr | Val | Leu | Val | Glu | Gly | |
| | | | 25 | | | | | 30 | | | | | 35 | | | |
| CAG | GCG | CTG | GGC | GGT | ACC | TGC | CTG | AAC | ATC | GGC | TGC | ATT | CCG | TCC | AAG | 4527 |
| Gln | Ala | Leu | Gly | Gly | Thr | Cys | Leu | Asn | Ile | Gly | Cys | Ile | Pro | Ser | Lys | |
| | | 40 | | | | | 45 | | | | | 50 | | | | |

| | | | | | | | | | | | | | | | | |
|---|---|---|---|---|---|---|---|---|---|---|---|---|---|---|---|---|
| GCG | CTG | ATC | CAT | GTG | GCC | GAG | CAG | TTC | CAC | CAG | GCC | TCG | CGC | TTT | ACC | 4575 |
| Ala | Leu | Ile | His | Val | Ala | Glu | Gln | Phe | His | Gln | Ala | Ser | Arg | Phe | Thr | |
| | | 55 | | | | 60 | | | | | 65 | | | | | |
| GAA | CCC | TCG | CCG | CTG | GGC | ATC | AGC | GTG | GCT | TCG | CCA | CGC | CTG | GAC | ATC | 4623 |
| Glu | Pro | Ser | Pro | Leu | Gly | Ile | Ser | Val | Ala | Ser | Pro | Arg | Leu | Asp | Ile | |
| 70 | | | | | 75 | | | | | 80 | | | | | 85 | |
| GGC | CAG | AGC | GTG | GCC | TGG | AAA | GAC | GGC | ATC | GTC | GAT | CGC | CTG | ACC | ACT | 4671 |
| Gly | Gln | Ser | Val | Ala | Trp | Lys | Asp | Gly | Ile | Val | Asp | Arg | Leu | Thr | Thr | |
| | | | | 90 | | | | | 95 | | | | | 100 | | |
| GGT | GTC | GCC | GCC | CTG | CTG | AAA | AAG | CAC | GGG | GTG | AAG | GTG | GTG | CAC | GGC | 4719 |
| Gly | Val | Ala | Ala | Leu | Leu | Lys | Lys | His | Gly | Val | Lys | Val | Val | His | Gly | |
| | | | 105 | | | | | 110 | | | | | 115 | | | |
| TGG | GCC | AAG | GTG | CTT | GAT | GGC | AAG | CAG | GTC | GAG | GTG | GAT | GGC | CAG | CGC | 4767 |
| Trp | Ala | Lys | Val | Leu | Asp | Gly | Lys | Gln | Val | Glu | Val | Asp | Gly | Gln | Arg | |
| | | 110 | | | | | 115 | | | | | 120 | | | | |
| ATC | CAG | TGC | GAG | CAC | CTG | TTG | CTG | GCC | ACG | GGC | TCC | AGC | AGT | GTC | GAA | 4815 |
| Ile | Gln | Cys | Glu | His | Leu | Leu | Leu | Ala | Thr | Gly | Ser | Ser | Ser | Val | Glu | |
| | 125 | | | | | 130 | | | | | 135 | | | | | |
| CTG | CCG | ATG | CTG | CCG | TTG | GGT | GGG | CCG | GTG | ATT | TCC | TCG | ACC | GAG | GCC | 4863 |
| Leu | Pro | Met | Leu | Pro | Leu | Gly | Gly | Pro | Val | Ile | Ser | Ser | Thr | Glu | Ala | |
| 140 | | | | | 145 | | | | | 150 | | | | | 155 | |
| CTG | GCA | CCG | AAA | GCC | CTG | CCG | CAA | CAC | CTG | GTG | GTG | GTG | GGC | GGT | GGC | 4911 |
| Leu | Ala | Pro | Lys | Ala | Leu | Pro | Gln | His | Leu | Val | Val | Val | Gly | Gly | Gly | |
| | | | | 160 | | | | | 165 | | | | | 170 | | |
| TAC | ATC | GGC | CTG | GAG | CTG | GGT | ATC | GCC | TAC | CGC | AAG | CTC | GGC | GCG | CAG | 4959 |
| Tyr | Ile | Gly | Leu | Glu | Leu | Gly | Ile | Ala | Tyr | Arg | Lys | Leu | Gly | Ala | Gln | |
| | | | 175 | | | | | 180 | | | | | 185 | | | |
| GTC | AGC | GTG | GTG | GAA | GCG | CGC | GAG | CGC | ATC | CTG | CCG | ACT | TAC | GAC | AGC | 5007 |
| Val | Ser | Val | Val | Glu | Ala | Arg | Glu | Arg | Ile | Leu | Pro | Thr | Tyr | Asp | Ser | |
| | | 190 | | | | | 195 | | | | | 200 | | | | |
| GAA | CTG | ACC | GCC | CCG | GTG | GCC | GAG | TCG | CTG | AAA | AAG | CTG | GGT | ATC | GCC | 5055 |
| Glu | Leu | Thr | Ala | Pro | Val | Ala | Glu | Ser | Leu | Lys | Lys | Leu | Gly | Ile | Ala | |
| 205 | | | | | 210 | | | | | 215 | | | | | | |
| CTG | CAC | CTT | GGC | CAC | AGC | GTC | GAA | GGT | TAC | GAA | AAT | GGC | TGC | CTG | CTG | 5103 |
| Leu | His | Leu | Gly | His | Ser | Val | Glu | Gly | Tyr | Glu | Asn | Gly | Cys | Leu | Leu | |
| 220 | | | | | 225 | | | | | 230 | | | | | 235 | |
| GCC | AAC | GAT | GGC | AAG | GGC | GGA | CAA | CTG | CGC | CTG | GAA | GCC | GAC | CGG | GTG | 5151 |
| Ala | Asn | Asp | Gly | Lys | Gly | Gly | Gln | Leu | Arg | Leu | Glu | Ala | Asp | Arg | Val | |
| | | | | 240 | | | | | 245 | | | | | 250 | | |
| CTG | GTG | GCC | GTG | GGC | CGC | CGC | CCA | CGC | ACC | AAG | GGC | TTC | AAC | CTG | GAA | 5199 |
| Leu | Val | Ala | Val | Gly | Arg | Arg | Pro | Arg | Thr | Lys | Gly | Phe | Asn | Leu | Glu | |
| | | | 255 | | | | | 260 | | | | | 265 | | | |
| TGC | CTG | GAC | CTG | AAG | ATG | AAT | GGT | GCC | GCG | ATT | GCC | ATC | GAC | GAG | CGC | 5247 |
| Cys | Leu | Asp | Leu | Lys | Met | Asn | Gly | Ala | Ala | Ile | Ala | Ile | Asp | Glu | Arg | |
| | | 270 | | | | | 275 | | | | | 280 | | | | |
| TGC | CAG | ACC | AGC | ATG | CAC | AAC | GTC | TGG | GCC | ATC | GGC | GAC | GTG | GCC | GGC | 5295 |
| Cys | Gln | Thr | Ser | Met | His | Asn | Val | Trp | Ala | Ile | Gly | Asp | Val | Ala | Gly | |
| | 285 | | | | | 290 | | | | | 295 | | | | | |
| GAA | CCG | ATG | CTG | GCG | CAC | CGG | GCC | ATG | GCC | CAG | GGC | GAG | ATG | GTG | GCC | 5343 |
| Glu | Pro | Met | Leu | Ala | His | Arg | Ala | Met | Ala | Gln | Gly | Glu | Met | Val | Ala | |
| 300 | | | | | 305 | | | | | 310 | | | | | 315 | |
| GAG | ATC | ATC | GCC | GGC | AAG | GCA | CGC | CGC | TTC | GAA | CCC | GCT | GCG | ATA | GCC | 5391 |
| Glu | Ile | Ile | Ala | Gly | Lys | Ala | Arg | Arg | Phe | Glu | Pro | Ala | Ala | Ile | Ala | |
| | | | | 320 | | | | | 325 | | | | | 330 | | |
| GCC | GTG | TGC | TTC | ACC | GAC | CCG | GAA | GTG | GTC | GTG | GTC | GGC | AAG | ACG | CCG | 5439 |
| Ala | Val | Cys | Phe | Thr | Asp | Pro | Glu | Val | Val | Val | Val | Gly | Lys | Thr | Pro | |
| | | | 335 | | | | | 340 | | | | | 345 | | | |
| GAA | CAG | GCC | AGT | CAG | CAA | GGC | CTG | GAC | TGC | ATC | GTC | GCG | CAG | TTC | CCG | 5487 |
| Glu | Gln | Ala | Ser | Gln | Gln | Gly | Leu | Asp | Cys | Ile | Val | Ala | Gln | Phe | Pro | |
| | | 350 | | | | | 355 | | | | | 360 | | | | |

| | | | | | | | | | | | | | | | | |
|---|---|---|---|---|---|---|---|---|---|---|---|---|---|---|---|---|
| TTC | GCC | GCC | AAC | GGC | CGG | GCC | ATG | AGC | CTG | GAG | TCG | AAA | AGC | GGT | TTC | 5535 |
| Phe | Ala | Ala | Asn | Gly | Arg | Ala | Met | Ser | Leu | Glu | Ser | Lys | Ser | Gly | Phe | |
| | 365 | | | | | 370 | | | | | 375 | | | | | |
| GTG | CGC | GTG | GTC | GCG | CGG | CGT | GAC | AAC | CAC | CTG | ATC | CTG | GGC | TGG | CAA | 5583 |
| Val | Arg | Val | Val | Ala | Arg | Arg | Asp | Asn | His | Leu | Ile | Leu | Gly | Trp | Gln | |
| 380 | | | | | 385 | | | | | 390 | | | | | 395 | |
| GCG | GTT | GGC | GTG | GCG | GTT | TCC | GAG | CTG | TCC | ACG | GCG | TTT | GCC | CAG | TCG | 5631 |
| Ala | Val | Gly | Val | Ala | Val | Ser | Glu | Leu | Ser | Thr | Ala | Phe | Ala | Gln | Ser | |
| | | | | 400 | | | | | 405 | | | | | 410 | | |
| CTG | GAG | ATG | GGT | GCC | TGC | CTG | GAG | GAT | GTG | GCC | GGT | ACC | ATC | CAT | GCC | 5679 |
| Leu | Glu | Met | Gly | Ala | Cys | Leu | Glu | Asp | Val | Ala | Gly | Thr | Ile | His | Ala | |
| | | | 415 | | | | | 420 | | | | | 425 | | | |
| CAC | CCG | ACC | CTG | GGT | GAA | GCG | GTA | CAG | GAA | GCG | GCA | CTG | CGT | GCC | CTG | 5727 |
| His | Pro | Thr | Leu | Gly | Glu | Ala | Val | Gln | Glu | Ala | Ala | Leu | Arg | Ala | Leu | |
| | | 430 | | | | | 435 | | | | | 440 | | | | |
| GGC | CAC | GCC | CTG | CAT | ATC | TGACACTGAA | GCGGCCGAGG | CCGATTTGGC | | | | | | | | 5775 |
| Gly | His | Ala | Leu | His | Ile | | | | | | | | | | | |
| | | 445 | | | | | | | | | | | | | | |

| | | | | | |
|---|---|---|---|---|---|
| CCGCCGCGCC | GAGAGGCGCT | GCGGGTCTTT | TTTATACCTG | TACCGGCAAA | CCAATTCACT | 5835 |
| CGGCGATGGC | ATTCTTGCNG | GCCCTTTTGG | CCCGGTACAT | TGCCTTATCA | GCCCNNNNCC | 5895 |
| AGNNGCGNAT | GCTNGGTCCT | CCCCTTCCTG | CCACTGCACC | ACGCCATAAC | TCATGGTCAG | 5955 |
| ACGGCACTCC | CCCACNGGTT | NCAGTTNNCG | CCATNCNNCC | NNGNAAGCGC | CCGGCGACAT | 6015 |
| CCAGCGCCTC | GCCCAGCGTG | CTCTGCGGCA | GTACGATAAC | GAACTCGTCC | CCGCCCCAGC | 6075 |
| GCGCCAACAG | GTCCATGTTC | GCGCAGGCAG | GTCCGCAGGC | TGTCGAC | | 6122 |

( 2 ) INFORMATION FOR SEQ ID NO:2:

( i ) SEQUENCE CHARACTERISTICS:
        ( A ) LENGTH: 409 Amino acids
        ( B ) TYPE: Amino acid
        ( D ) TOPOLOGY: Linear ( i i ) MOLECULE TYPE: Protein ( i x ) FEATURE:
        ( A ) NAME/KEY: Alpha subunit of E1 component
        ( B ) LOCATION: 805-2031, Does not include initiating methionine
        ( C ) IDENTIFICATION METHOD: N- terminal amino acid sequence ( x ) PUBLICATION INFORMATION:
        ( A ) AUTHORS: Burns, Gayle
                       Brown, Tracy
                       Hatter, Kenneth
                       Idriss, John. M.
                       Sokatch, John R.
        ( B ) TITLE: Similarity of the E1 subunits of branched-chain
               oxoacid dehydrogenase from Pseudomonas putida to the
               corresponding subunits of mammalian branched-chain-oxoacid
               and pyruvate dehydrogenases
        ( C ) JOURNAL: European Journal of Biochemistry
        ( D ) VOLUME: 176
        ( F ) PAGES: 311-317
        ( G ) DATE: 1988

( x i ) SEQUENCE DESCRIPTION: SEQ ID NO:2:

| | | | | | | | | | | | | | | |
|---|---|---|---|---|---|---|---|---|---|---|---|---|---|---|
| Asn | Glu | Tyr | Ala | Pro | Leu | Arg | Leu | His | Val | Pro | Glu | Pro | Thr | Gly |
| | | | | 5 | | | | | 10 | | | | | 15 |
| Arg | Pro | Gly | Cys | Gln | Thr | Asp | Phe | Ser | Tyr | Leu | Arg | Leu | Asn | Asp |
| | | | | 20 | | | | | 25 | | | | | 30 |
| Ala | Gly | Gln | Ala | Arg | Lys | Pro | Pro | Val | Asp | Val | Asp | Ala | Ala | Asp |
| | | | | 35 | | | | | 40 | | | | | 45 |
| Thr | Ala | Asp | Leu | Ser | Tyr | Ser | Leu | Val | Arg | Val | Leu | Asp | Glu | Gln |
| | | | | 50 | | | | | 55 | | | | | 60 |

| | | | | | | | | | | | | | | |
|---|---|---|---|---|---|---|---|---|---|---|---|---|---|---|
|Gly|Asp|Ala|Gln|Gly<br>65|Pro|Trp|Ala|Glu|Asp<br>70|Ile|Asp|Pro|Gln|Ile<br>75|
|Leu|Arg|Gln|Gly|Met<br>80|Arg|Ala|Met|Leu|Lys<br>85|Thr|Arg|Ile|Phe|Asp<br>90|
|Ser|Arg|Met|Val|Val<br>95|Ala|Gln|Arg|Gln|Lys<br>100|Lys|Met|Ser|Phe|Tyr<br>105|
|Met|Gln|Ser|Leu|Gly<br>110|Glu|Glu|Ala|Ile|Gly<br>115|Ser|Gly|Gln|Ala|Leu<br>120|
|Ala|Leu|Asn|Arg|Thr<br>125|Asp|Met|Cys|Phe|Pro<br>130|Thr|Tyr|Arg|Gln|Gln<br>135|
|Ser|Ile|Leu|Met|Ala<br>140|Arg|Asp|Val|Ser|Leu<br>145|Val|Glu|Met|Ile|Cys<br>150|
|Gln|Leu|Leu|Ser|Asn<br>155|Glu|Arg|Asp|Pro|Leu<br>160|Lys|Gly|Arg|Gln|Leu<br>165|
|Pro|Ile|Met|Tyr|Ser<br>170|Val|Arg|Glu|Ala|Gly<br>175|Phe|Phe|Thr|Ile|Ser<br>180|
|Gly|Asn|Leu|Ala|Thr<br>185|Gln|Phe|Val|Gln|Ala<br>190|Val|Gly|Trp|Ala|Met<br>195|
|Ala|Ser|Ala|Ile|Lys<br>200|Gly|Asp|Thr|Lys|Ile<br>205|Ala|Ser|Ala|Trp|Ile<br>210|
|Gly|Asp|Gly|Ala|Thr<br>215|Ala|Glu|Ser|Asp|Phe<br>220|His|Thr|Ala|Leu|Thr<br>225|
|Phe|Ala|His|Val|Tyr<br>230|Arg|Ala|Pro|Val|Ile<br>235|Leu|Asn|Val|Val|Asn<br>240|
|Asn|Gln|Trp|Ala|Ile<br>245|Ser|Thr|Phe|Gln|Ala<br>250|Ile|Ala|Gly|Gly|Glu<br>255|
|Ser|Thr|Thr|Phe|Ala<br>260|Gly|Arg|Gly|Val|Gly<br>265|Cys|Gly|Ile|Ala|Ser<br>270|
|Leu|Arg|Val|Asp|Gly<br>275|Asn|Asp|Phe|Val|Ala<br>280|Val|Tyr|Ala|Ala|Ser<br>285|
|Arg|Trp|Ala|Ala|Glu<br>290|Arg|Ala|Arg|Arg|Gly<br>295|Leu|Gly|Pro|Ser|Leu<br>300|
|Ile|Glu|Trp|Val|Thr<br>305|Tyr|Arg|Ala|Gly|Pro<br>310|His|Ser|Thr|Ser|Asp<br>315|
|Asp|Pro|Ser|Lys|Tyr<br>320|Arg|Pro|Ala|Asp|Asp<br>325|Trp|Ser|His|Phe|Pro<br>330|
|Leu|Gly|Asp|Pro|Ile<br>335|Ala|Arg|Leu|Lys|Gln<br>340|His|Leu|Ile|Lys|Ile<br>345|
|Gly|His|Trp|Cys|Glu<br>350|Glu|Glu|His|Gln|Ala<br>355|Thr|Thr|Ala|Glu|Phe<br>360|
|Glu|Ala|Ala|Val|Ile<br>365|Ala|Ala|Gln|Lys|Glu<br>370|Ala|Glu|Gln|Tyr|Gly<br>375|
|Thr|Leu|Ala|Asn|Gly<br>380|His|Ile|Pro|Ser|Ala<br>385|Ala|Ser|Met|Phe|Glu<br>390|
|Asp|Val|Tyr|Lys|Glu<br>395|Met|Pro|Asp|His|Leu<br>400|Arg|Arg|Gln|Arg|Gln<br>405|
|Glu|Leu|Gly|Val| | | | | | | | | | | |

( 2 ) INFORMATION FOR SEQ ID NO:3:

( i ) SEQUENCE CHARACTERISTICS:
        ( A ) LENGTH: 338 Amino acids
        ( B ) TYPE: Amino acid
        ( D ) TOPOLOGY: Linear ( i i ) MOLECULE TYPE: Protein ( i x ) FEATURE:
    ( A ) NAME/KEY: Beta subunit of E1 component
    ( B ) LOCATION: 2078-3091, Does not include inidiating
        methionine
    ( C ) IDENTIFICATION METHOD: N- terminal amino acid sequence ( x ) PUBLICATION INFORMATION:
    ( A ) AUTHORS: Burns, Gayle
        Brown, Tracy
        Hatter, Kenneth
        Idriss, John M.
        Sokatch, John R.
    ( B ) TITLE: Similarity of the E1 subunits of branched-chain-
        oxoacid dehydrogenase from Pseudomonas putida to the
        corresponding subunits of mammalian branched-chain-oxoacid
        and pyruvate dehydrogenases
    ( C ) JOURNAL: European Journal of Biochemistry
    ( D ) VOLUME: 176
    ( F ) PAGES: 31-317
    ( G ) DATE: 1988

( x i ) SEQUENCE DESCRIPTION: SEQ ID NO:3:

| Ala | Thr | Thr | Thr | Met | Thr | Met | Ile | Gln | Ala | Leu | Arg | Ser | Ala | Met |
|-----|-----|-----|-----|-----|-----|-----|-----|-----|-----|-----|-----|-----|-----|-----|
|     |     |     |     | 5   |     |     |     |     | 10  |     |     |     |     | 15  |
| Asp | Val | Met | Leu | Glu | Arg | Asp | Asp | Asn | Val | Val | Tyr | Gly | Gln |
|     |     |     |     | 20  |     |     |     |     | 25  |     |     |     |     | 30  |
| Asp | Val | Gly | Tyr | Phe | Gly | Gly | Val | Phe | Arg | Cys | Thr | Glu | Gly | Leu |
|     |     |     |     | 35  |     |     |     |     | 40  |     |     |     |     | 45  |
| Gln | Thr | Lys | Tyr | Gly | Lys | Ser | Arg | Val | Phe | Asp | Ala | Pro | Ile | Ser |
|     |     |     |     | 50  |     |     |     |     | 55  |     |     |     |     | 60  |
| Glu | Ser | Gly | Ile | Val | Gly | Thr | Ala | Val | Gly | Met | Gly | Ala | Tyr | Gly |
|     |     |     |     | 65  |     |     |     |     | 70  |     |     |     |     | 75  |
| Leu | Arg | Pro | Val | Val | Glu | Ile | Gln | Phe | Ala | Asp | Tyr | Phe | Tyr | Pro |
|     |     |     |     | 80  |     |     |     |     | 85  |     |     |     |     | 90  |
| Ala | Ser | Asp | Gln | Ile | Val | Ser | Glu | Met | Ala | Arg | Leu | Arg | Tyr | Arg |
|     |     |     |     | 95  |     |     |     |     | 100 |     |     |     |     | 105 |
| Ser | Ala | Gly | Glu | Phe | Ile | Ala | Pro | Leu | Thr | Leu | Arg | Met | Pro | Cys |
|     |     |     |     | 110 |     |     |     |     | 115 |     |     |     |     | 120 |
| Gly | Gly | Gly | Ile | Tyr | Gly | Gly | Gln | Thr | His | Ser | Gln | Ser | Pro | Glu |
|     |     |     |     | 125 |     |     |     |     | 130 |     |     |     |     | 135 |
| Ala | Met | Phe | Thr | Gln | Val | Cys | Gly | Leu | Arg | Thr | Val | Met | Pro | Ser |
|     |     |     |     | 140 |     |     |     |     | 145 |     |     |     |     | 150 |
| Asn | Pro | Tyr | Asp | Ala | Lys | Gly | Leu | Leu | Ile | Ala | Ser | Ile | Glu | Cys |
|     |     |     |     | 155 |     |     |     |     | 160 |     |     |     |     | 165 |
| Asp | Asp | Pro | Val | Ile | Phe | Leu | Glu | Pro | Lys | Arg | Leu | Tyr | Asn | Gly |
|     |     |     |     | 170 |     |     |     |     | 175 |     |     |     |     | 180 |
| Pro | Phe | Asp | Gly | His | His | Asp | Arg | Pro | Val | Thr | Pro | Trp | Ser | Lys |
|     |     |     |     | 185 |     |     |     |     | 190 |     |     |     |     | 195 |
| His | Pro | His | Ser | Ala | Val | Pro | Asp | Gly | Tyr | Tyr | Thr | Val | Pro | Leu |
|     |     |     |     | 200 |     |     |     |     | 205 |     |     |     |     | 210 |
| Asp | Lys | Ala | Ala | Ile | Thr | Arg | Pro | Gly | Asn | Asp | Val | Ser | Val | Leu |
|     |     |     |     | 215 |     |     |     |     | 220 |     |     |     |     | 225 |
| Thr | Tyr | Gly | Thr | Thr | Val | Tyr | Val | Ala | Gln | Val | Ala | Ala | Glu | Glu |
|     |     |     |     | 230 |     |     |     |     | 235 |     |     |     |     | 240 |
| Ser | Gly | Val | Asp | Ala | Glu | Val | Ile | Asp | Leu | Arg | Ser | Leu | Trp | Pro |
|     |     |     |     | 245 |     |     |     |     | 250 |     |     |     |     | 255 |
| Leu | Asp | Leu | Asp | Thr | Ile | Val | Glu | Ser | Val | Lys | Lys | Thr | Gly | Arg |
|     |     |     |     | 260 |     |     |     |     | 265 |     |     |     |     | 270 |
| Cys | Val | Val | Val | His | Glu | Ala | Thr | Arg | Thr | Cys | Gly | Phe | Gly | Ala |
|     |     |     |     | 275 |     |     |     |     | 280 |     |     |     |     | 285 |

| | | | | | | | | | | | | | | | |
|---|---|---|---|---|---|---|---|---|---|---|---|---|---|---|---|
|Glu|Leu|Val|Ser|Leu<br>290|Val|Gln|Glu|His|Cys<br>295|Phe|His|His|Leu|Glu<br>300||
|Ala|Pro|Ile|Glu|Arg<br>305|Val|Thr|Gly|Trp|Asp<br>310|Thr|Pro|Tyr|Pro|His<br>315||
|Ala|Gln|Glu|Trp|Ala<br>320|Tyr|Phe|Pro|Gly|Pro<br>325|Ser|Arg|Val|Gly|Ala<br>330||
|Ala|Leu|Lys|Lys|Val<br>335|Met|Glu|Val| | | | | | | ||

( 2 ) INFORMATION FOR SEQ ID NO:4:

( i ) SEQUENCE CHARACTERISTICS:
        ( A ) LENGTH: 422 Amino acids
        ( B ) TYPE: Amino acid
        ( D ) TOPOLOGY: Linear ( i i ) MOLECULE TYPE: Protein ( i x ) FEATURE:
        ( A ) NAME/KEY: E2 component
        ( B ) LOCATION: 3098-4363, does not include initiating methionine
        ( C ) IDENTIFICATION METHOD: N- terminal sequence ( x ) PUBLICATION INFORMATION:
        ( A ) AUTHORS: Burns, Gayle
                        Brown, Tracy
                        Hatter, Kenneth
                        Sokatch, John R.
        ( B ) TITLE: Compaarison of the amion acid sequences of the transacylase components of branched-chain oxoacid dehydrogenase of Pseudomonas putida, and the pyruvate and 2-oxoglutarate dehydrogenases of Escherichia coli
        ( C ) JOURNAL: European Journal of Biochemistry
        ( D ) VOLUME: 176
        ( F ) PAGES: 165-169
        ( D ) DATE: 1988

( x i ) SEQUENCE DESCRIPTION: SEQ ID NO:4:

| | | | | | | | | | | | | | | |
|---|---|---|---|---|---|---|---|---|---|---|---|---|---|---|
|Gly|Thr|His|Val|Ile<br>5|Lys|Met|Pro|Asp|Ile<br>10|Gly|Glu|Gly|Ile|Ala<br>15|
|Gln|Val|Glu|Leu|Val<br>20|Glu|Trp|Phe|Val|Lys<br>25|Val|Gly|Asp|Ile|Ile<br>30|
|Ala|Glu|Asp|Gln|Val<br>35|Val|Ala|Asp|Val|Met<br>40|Thr|Asp|Lys|Ala|Thr<br>45|
|Val|Glu|Ile|Pro|Ser<br>50|Pro|Val|Ser|Gly|Lys<br>55|Val|Leu|Ala|Leu|Gly<br>60|
|Gly|Gln|Pro|Gly|Glu<br>65|Val|Met|Ala|Val|Gly<br>70|Ser|Glu|Leu|Ile|Arg<br>75|
|Ile|Glu|Val|Glu|Gly<br>80|Ser|Gly|Asn|His|Val<br>85|Asp|Val|Pro|Gln|Ala<br>90|
|Lys|Pro|Ala|Glu|Val<br>95|Pro|Ala|Ala|Pro|Val<br>100|Ala|Ala|Lys|Pro|Glu<br>105|
|Pro|Gln|Lys|Asp|Val<br>110|Lys|Pro|Ala|Ala|Tyr<br>115|Gln|Ala|Ser|Ala|Ser<br>120|
|His|Glu|Ala|Ala|Pro<br>125|Ile|Val|Pro|Arg|Gln<br>130|Pro|Gly|Asp|Lys|Pro<br>135|
|Leu|Ala|Ser|Pro|Ala<br>140|Val|Arg|Lys|Arg|Ala<br>145|Leu|Asp|Ala|Gly|Ile<br>150|
|Glu|Leu|Arg|Tyr|Val<br>155|His|Gly|Ser|Gly|Pro<br>160|Ala|Gly|Arg|Ile|Leu<br>165|
|His|Glu|Asp|Leu|Asp<br>170|Ala|Phe|Met|Ser|Lys<br>175|Pro|Gln|Ser|Ala|Ala<br>180|

| | | | | | | | | | | | | | |
|---|---|---|---|---|---|---|---|---|---|---|---|---|---|
| Gly | Gln | Thr | Pro | Asn<br>185 | Gly | Tyr | Ala | Arg | Arg<br>190 | Thr | Asp | Ser | Glu | Gln<br>195 |
| Val | Pro | Val | Ile | Gly<br>200 | Leu | Arg | Arg | Lys | Ile<br>205 | Ala | Gln | Arg | Met | Gln<br>210 |
| Asp | Ala | Lys | Arg | Arg<br>215 | Val | Ala | His | Phe | Ser<br>220 | Tyr | Val | Glu | Glu | Ile<br>225 |
| Asp | Val | Thr | Ala | Leu<br>230 | Glu | Ala | Leu | Arg | Gln<br>235 | Gln | Leu | Asn | Ser | Lys<br>240 |
| His | Gly | Asp | Ser | Arg<br>245 | Gly | Lys | Leu | Thr | Leu<br>250 | Leu | Pro | Phe | Leu | Val<br>255 |
| Arg | Ala | Leu | Val | Val<br>260 | Ala | Leu | Arg | Asp | Phe<br>265 | Pro | Gln | Ile | Asn | Ala<br>270 |
| Thr | Tyr | Asp | Asp | Glu<br>275 | Ala | Gln | Ile | Ile | Thr<br>280 | Arg | His | Gly | Ala | Val<br>285 |
| His | Val | Gly | Ile | Ala<br>290 | Thr | Gln | Gly | Asp | Asn<br>295 | Gly | Leu | Met | Val | Pro<br>300 |
| Val | Leu | Arg | His | Ala<br>305 | Glu | Ala | Gly | Ser | Leu<br>310 | Trp | Ala | Asn | Ala | Gly<br>315 |
| Glu | Ile | Ser | Arg | Leu<br>320 | Ala | Asn | Ala | Ala | Arg<br>325 | Asn | Asn | Lys | Ala | Ser<br>330 |
| Arg | Glu | Glu | Leu | Ser<br>335 | Gly | Ser | Thr | Ile | Thr<br>340 | Leu | Thr | Ser | Leu | Gly<br>345 |
| Ala | Leu | Gly | Gly | Ile<br>350 | Val | Ser | Thr | Pro | Val<br>355 | Val | Asn | Thr | Pro | Glu<br>360 |
| Val | Ala | Ile | Val | Gly<br>365 | Val | Asn | Arg | Met | Val<br>370 | Glu | Arg | Pro | Val | Val<br>375 |
| Ile | Asp | Gly | Gln | Ile<br>380 | Val | Val | Arg | Lys | Met<br>385 | Met | Asn | Leu | Ser | Ser<br>390 |
| Ser | Phe | Asp | His | Arg<br>395 | Val | Val | Asp | Gly | Met<br>400 | Asp | Ala | Ala | Leu | Phe<br>405 |
| Ile | Gln | Ala | Val | Arg<br>410 | Gly | Leu | Leu | Glu | Gln<br>415 | Pro | Ala | Cys | Leu | Phe<br>420 |
| Val | Glu | | | | | | | | | | | | | |

(2) INFORMATION FOR SEQ ID NO:5:

( i ) SEQUENCE CHARACTERISTICS:
        ( A ) LENGTH: 459 Amino acids
        ( B ) TYPE: Amino acid
        ( D ) TOPOLOGY: Linear ( i i i ) MOLECULE TYPE: Protein ( i x ) FEATURE:
        ( A ) NAME/KEY: Lpd-val, the E3 component
        ( B ) LOCATION: 4369-5745, N-terminal methionine is present on
            mature protein
        ( C ) IDENTIFICATION METHOD: Sequence of cyanogen bromide
            peptides ( x ) PUBLICATION INFORMATION:
        ( A ) AUTHORS: Burns, Gayle
            Brown, Tracy
            Hatter, Kenneth
            Sokatch, John R.
        ( B ) TITLE: Sequence analysis of the lpdV gene for lipoamide
            dehodrogenase of Pseudomonas putida
        ( C ) JOURNAL: European Journal of Biochemistry
        ( D ) VOLUME: 179
        ( F ) PAGES: 61-69
        ( G ) DATE: 1989

( x i ) SEQUENCE DESCRIPTION: SEQ ID NO:5:

| | | | | | | | | | | | | | | |
|---|---|---|---|---|---|---|---|---|---|---|---|---|---|---|
| Met | Gln | Gln | Thr | Ile | Gln | Thr | Thr | Leu | Leu | Ile | Ile | Gly | Gly | Gly |
| | | | | 5 | | | | 10 | | | | | | 15 |
| Pro | Gly | Gly | Tyr | Val | Ala | Ala | Ile | Arg | Ala | Gly | Gln | Leu | Gly | Ile |
| | | | | 20 | | | | 25 | | | | | | 30 |
| Pro | Thr | Val | Leu | Val | Glu | Gly | Gln | Ala | Leu | Gly | Gly | Thr | Cys | Leu |
| | | | | 35 | | | | 40 | | | | | | 45 |
| Asn | Ile | Gly | Cys | Ile | Pro | Ser | Lys | Ala | Leu | Ile | His | Val | Ala | Glu |
| | | | | 50 | | | | 55 | | | | | | 60 |
| Gln | Phe | His | Gln | Ala | Ser | Arg | Phe | Thr | Glu | Pro | Ser | Pro | Leu | Gly |
| | | | | 65 | | | | 70 | | | | | | 75 |
| Ile | Ser | Val | Ala | Ser | Pro | Arg | Leu | Asp | Ile | Gly | Gln | Ser | Val | Ala |
| | | | | 80 | | | | 85 | | | | | | 90 |
| Trp | Lys | Asp | Gly | Ile | Val | Asp | Arg | Leu | Thr | Thr | Gly | Val | Ala | Ala |
| | | | | 95 | | | | 100 | | | | | | 105 |
| Leu | Leu | Lys | Lys | His | Gly | Val | Lys | Val | His | Gly | Trp | Ala | Lys |
| | | | | 110 | | | | 115 | | | | | 120 |
| Val | Leu | Asp | Gly | Lys | Gln | Val | Glu | Val | Asp | Gly | Gln | Arg | Ile | Gln |
| | | | | 125 | | | | 130 | | | | | | 135 |
| Cys | Glu | His | Leu | Leu | Leu | Ala | Thr | Gly | Ser | Ser | Ser | Val | Glu | Leu |
| | | | | 140 | | | | 145 | | | | | | 150 |
| Pro | Met | Leu | Pro | Leu | Gly | Gly | Pro | Val | Ile | Ser | Ser | Thr | Glu | Ala |
| | | | | 155 | | | | 160 | | | | | | 165 |
| Leu | Ala | Pro | Lys | Ala | Leu | Pro | Gln | His | Leu | Val | Val | Val | Gly | Gly |
| | | | | 170 | | | | 175 | | | | | | 180 |
| Gly | Tyr | Ile | Gly | Leu | Glu | Leu | Gly | Ile | Ala | Tyr | Arg | Lys | Leu | Gly |
| | | | | 185 | | | | 190 | | | | | | 195 |
| Ala | Gln | Val | Ser | Val | Val | Glu | Ala | Arg | Glu | Arg | Ile | Leu | Pro | Thr |
| | | | | 200 | | | | 205 | | | | | | 210 |
| Tyr | Asp | Ser | Glu | Leu | Thr | Ala | Pro | Val | Ala | Glu | Ser | Leu | Lys | Lys |
| | | | | 215 | | | | 220 | | | | | | 225 |
| Leu | Gly | Ile | Ala | Leu | His | Leu | Gly | His | Ser | Val | Glu | Gly | Tyr | Glu |
| | | | | 230 | | | | 235 | | | | | | 240 |
| Asn | Gly | Cys | Leu | Leu | Ala | Asn | Asp | Gly | Lys | Gly | Gly | Gln | Leu | Arg |
| | | | | 245 | | | | 250 | | | | | | 255 |
| Leu | Glu | Ala | Asp | Arg | Val | Leu | Val | Ala | Val | Gly | Arg | Arg | Pro | Arg |
| | | | | 260 | | | | 265 | | | | | | 270 |
| Thr | Lys | Gly | Phe | Asn | Leu | Glu | Cys | Leu | Asp | Leu | Lys | Met | Asn | Gly |
| | | | | 275 | | | | 280 | | | | | | 285 |
| Ala | Ala | Ile | Ala | Ile | Asp | Glu | Arg | Cys | Gln | Thr | Ser | Met | His | Asn |
| | | | | 290 | | | | 295 | | | | | | 300 |
| Val | Trp | Ala | Ile | Gly | Asp | Val | Ala | Gly | Glu | Pro | Met | Leu | Ala | His |
| | | | | 305 | | | | 310 | | | | | | 315 |
| Arg | Ala | Met | Ala | Gln | Gly | Glu | Met | Val | Ala | Glu | Ile | Ile | Ala | Gly |
| | | | | 320 | | | | 325 | | | | | | 330 |
| Lys | Ala | Arg | Arg | Phe | Glu | Pro | Ala | Ala | Ile | Ala | Ala | Val | Cys | Phe |
| | | | | 335 | | | | 340 | | | | | | 345 |
| Thr | Asp | Pro | Glu | Val | Val | Val | Val | Gly | Lys | Thr | Pro | Glu | Gln | Ala |
| | | | | 350 | | | | 355 | | | | | | 360 |
| Ser | Gln | Gln | Gly | Leu | Asp | Cys | Ile | Val | Ala | Gln | Phe | Pro | Phe | Ala |
| | | | | 365 | | | | 370 | | | | | | 375 |
| Ala | Asn | Gly | Arg | Ala | Met | Ser | Leu | Glu | Ser | Lys | Ser | Gly | Phe | Val |
| | | | | 380 | | | | 385 | | | | | | 390 |

| Arg | Val | Val | Ala | Arg<br>395 | Arg | Asp | Asn | His | Leu<br>400 | Ile | Leu | Gly | Trp | Gln<br>405 |
|---|---|---|---|---|---|---|---|---|---|---|---|---|---|---|
| Ala | Val | Gly | Val | Ala<br>410 | Val | Ser | Glu | Leu | Ser<br>415 | Thr | Ala | Phe | Ala | Gln<br>420 |
| Ser | Leu | Glu | Met | Gly<br>425 | Ala | Cys | Leu | Glu | Asp<br>430 | Val | Ala | Gly | Thr | Ile<br>435 |
| His | Ala | His | Pro | Thr<br>440 | Leu | Gly | Glu | Ala | Val<br>445 | Gln | Glu | Ala | Ala | Leu<br>450 |
| Arg | Ala | Leu | Gly | His<br>455 | Ala | Leu | His | Ile | | | | | | |

( 2 ) INFORMATION FOR SEQ ID NO:6:

( i ) SEQUENCE CHARACTERISTICS:
        ( A ) LENGTH: 792 Base pairs
        ( B ) TYPE: Nucleic acid
        ( C ) STRANDEDNESS: Double- stranded
        ( D ) TOPOLOGY: Circular ( i i ) MOLECULE TYPE: Nucleic acid ( i x ) FEATURE:
        ( A ) NAME/KEY: Control region regulating expression of the bkd
            operon
        ( B ) LOCATION: 1-792
        ( C ) IDENTIFICATION METHOD: S1 nuclease and reverse
            transcriptase mapping ( x ) PUBLICATION INFORMATION:
        ( A ) AUTHORS: Madhusudhan, K.T.
            Huang, G.
            Burns, Gayle
            Sokatch, John R.
        ( B ) TITLE: Transcriptional analysis of the promoter region of
            the branched chain keto acid dehydrogenase operon of
            Pseudomonas putida
        ( C ) JOURNAL: Journal of Bacteriology
        ( D ) VOLUME: 172
        ( F ) PAGES: 5655-5663
        ( G ) DATE: 1990

( x i ) SEQUENCE DESCRIPTION: SEQ ID NO:6:

```
CGATGCCCTG GAGCTGAGCG ATGCTCATGA CGCTTGTCCT TGTTGTTGTA GGCTGACAAC      60
AACATAGGCT GGGGGTGTTT AAAATATCAA GCAGCCTCTC GAACGCCTGG GGCCTCTTCT     120
ATCGCGCAAG GTCATGCCAT TGGCCGGCAA CGGCAAGGCT GTCTTGTAGC GCACCTGTTT     180
CAAGGCAAAA CTCGAGCGGA TATTCGCCAC ACCCGGCAAC CGGGTCAGGT AATCGAGAAA     240
CCGCTCCAGC GCCTGGATAC TCGGCAGCAG TACCCGCAAC AGGTAGTCCG GGTCGCCCGT     300
CATCAGGTAG CACTCCATCA CCTCGGGCCG TTCGGCAATT TCTTCCTCGA AGCGGTGCAG     360
CGACTGCTCT ACCTGTTTTT CCAGGCTGAC ATGGATGAAC ACATTCACAT CCAGCCCCAA     420
CGCCTCGGGC GACAACAAGG TCACCTGCTG GCGGATCACC CCCAGTTCTT CCATGGCCCG     480
CACCCGGTTG AAACAGGGCG TGGGCGACAG GTTGACCGAG CGTGCCAGCT CGGCGTTGGT     540
GATGCGGGCG TTTTCCTGCA GGCTGTTGAG AATGCCGATA TCGGTACGAT CGAGTTTGCG     600
CATGAGACAA AATCACCGGT TTTTGTGTT  TATGCGGAAT GTTATCTGC  CCCGCTCGGC     660
AAAGGCAATC AACTTGAGAG AAAAATTCTC CTGCCGGACC ACTAAGATGT AGGGGACGCT     720
GACTTACCAG TCACAAGCCG GTACTCAGCG GCGGCCGCTT CAGAGCTCAC AAAAACAAAT     780
ACCCGAGCGA GC                                                        792
```

( 2 ) INFORMATION FOR SEQ ID NO:7:

( i ) SEQUENCE CHARACTERISTICS:

(A) LENGTH: 15 Bases
(B) TYPE: Nucleic acid
(C) STRANDEDNESS: Single stranded
(D) TOPOLOGY: Linear (ii) MOLECULE TYPE: Nucleic acid
(A) DESCRIPTION: Seq ID No:7 is a synthetic nucleic acid used
to determine the transcriptional start of the bkd operon.

(ix) FEATURE:
(A) NAME/KEY: Synthetic nucleic acid used to determine the
transcriptional start of the bkd operon by primer
extension from the 3'end.
(B) LOCATION: Complementary to bases 256-270 of Seq ID No:1

(x) PUBLICATION INFORMATION:
(A) AUTHORS: Madhusudhan,K.T.
Huang,G.
Burns,G.
Sokatch,John R.
(B) TITLE: Transcriptional analysis of the promoter region of
the branched chain keto acid dehydrogenase operon of
Pseudomonas putida
(C) JOURNAL: Journal of Bacteriology
(D) VOLUME: 172
(F) PAGES: 5655-5663
(G) DATE: 1990

(xi) SEQUENCE DESCRIPTION: SEQ ID NO:7:

CTGCTGCCGA GTATC 15

What is claimed is:

1. A recombinant DNA molecule comprising a sequence comprising the following elements in the 5' to 3' direction, said elements which are operably linked:

genes encoding all the subunits of branched chain keto acid dehydrogenase complex of *Pseudomonas putida*.

2. The recombinant DNA molecule of claim 1 comprising DNA encoding SEQ ID NO:2, 3, 4, and 5.

3. A plasmid comprising the DNA molecule of claim 1.

4. A transformant bacterial host comprising the plasmid of claim 3.

* * * * *